(12) United States Patent
Yu et al.

(10) Patent No.: US 11,364,007 B2
(45) Date of Patent: Jun. 21, 2022

(54) OPTIMIZED SCANNING METHODS AND TOMOGRAPHY SYSTEM USING REGION OF INTEREST DATA

(71) Applicant: Accuray, Inc., Sunnyvale, CA (US)

(72) Inventors: Zhicong Yu, Highland Hts., OH (US); Amit Jain, Solon, OH (US); Daniel Gagnon, Twinsburg, OH (US); Jacob Shea, Madison, WI (US)

(73) Assignee: Accuray, Inc., Sunnyvale, CA (US)

( * ) Notice: Subject to any disclaimer, the term of this patent is extended or adjusted under 35 U.S.C. 154(b) by 172 days.

(21) Appl. No.: 16/694,177

(22) Filed: Nov. 25, 2019

(65) Prior Publication Data
US 2020/0170596 A1    Jun. 4, 2020

Related U.S. Application Data

(60) Provisional application No. 62/878,364, filed on Jul. 25, 2019, provisional application No. 62/843,796, (Continued)

(51) Int. Cl.
*A61B 6/00* (2006.01)
*G06T 11/00* (2006.01)
(Continued)

(52) U.S. Cl.
CPC ............ *A61B 6/5282* (2013.01); *A61B 6/027* (2013.01); *A61B 6/032* (2013.01); *A61B 6/06* (2013.01);
(Continued)

(58) Field of Classification Search
None
See application file for complete search history.

(56) References Cited

U.S. PATENT DOCUMENTS 4,190,773 A     2/1980   Braden
5,615,279 A     3/1997   Yoshioka et al.
(Continued)

FOREIGN PATENT DOCUMENTS

DE   10 2006 007058 A1   7/2007
EP         1062914 A1   12/2000
(Continued)

OTHER PUBLICATIONS

Office Action from U.S. Appl. No. 16/694,145 dated Mar. 17, 2021 (10 pages).
(Continued)

*Primary Examiner* — Hoon K Song
(74) *Attorney, Agent, or Firm* — Calfee, Halter & Griswold LLP

(57) ABSTRACT

A method of scanning parameter optimization, which method may be useful with image-guided radiation therapy (IGRT), allows for controlling exposure of a beam from an x-ray source and/or controlling the detection mechanism for an x-ray detector of imaging radiation of a radiation-delivery device based on one or more parameters of a region of interest of a patient. The one or more parameters of the region of interest may include a dimension, outer contour, density, location relative to an outlet of the beam, location relative to isocenter, location to the whole patient body, etc. Exposure of the patient to the beam may be varied via modulation of one or more scanning parameters for controlling an aspect of the beam and/or the detector to provide for targeted and or reduced radiation exposure of the patient or portion of the patient, and/or for improved quality of guiding images. The modulation may be varied depending on a view angle of the region of interest from a portion of the radiation-delivery device.

11 Claims, 7 Drawing Sheets

Related U.S. Application Data filed on May 6, 2019, provisional application No. 62/836,357, filed on Apr. 19, 2019, provisional application No. 62/836,352, filed on Apr. 19, 2019, provisional application No. 62/821,116, filed on Mar. 20, 2019, provisional application No. 62/813,335, filed on Mar. 4, 2019, provisional application No. 62/801,260, filed on Feb. 5, 2019, provisional application No. 62/800,287, filed on Feb. 1, 2019, provisional application No. 62/796,831, filed on Jan. 25, 2019, provisional application No. 62/773,700, filed on Nov. 30, 2018, provisional application No. 62/773,712, filed on Nov. 30, 2018.

(51) Int. Cl.

| | |
|---|---|
| *A61B 6/03* | (2006.01) |
| *A61B 6/06* | (2006.01) |
| *A61B 6/02* | (2006.01) |
| *A61N 5/10* | (2006.01) |
| *A61B 6/08* | (2006.01) |
| *G06T 7/30* | (2017.01) |
| *A61B 5/055* | (2006.01) |
| *A61B 6/04* | (2006.01) |

(52) U.S. Cl.

CPC ............ *A61B 6/405* (2013.01); *A61B 6/4078* (2013.01); *A61B 6/4085* (2013.01); *A61B 6/469* (2013.01); *A61B 6/488* (2013.01); *A61B 6/5205* (2013.01); *G06T 11/005* (2013.01); *A61B 5/055* (2013.01); *A61B 6/025* (2013.01); *A61B 6/03* (2013.01); *A61B 6/035* (2013.01); *A61B 6/0407* (2013.01); *A61B 6/08* (2013.01); *A61B 6/4014* (2013.01); *A61B 6/4021* (2013.01); *A61B 6/4028* (2013.01); *A61B 6/4064* (2013.01); *A61B 6/4435* (2013.01); *A61B 6/4441* (2013.01); *A61B 6/4458* (2013.01); *A61B 6/481* (2013.01); *A61B 6/482* (2013.01); *A61B 6/483* (2013.01); *A61B 6/484* (2013.01); *A61B 6/541* (2013.01); *A61B 6/582* (2013.01); *A61N 5/107* (2013.01); *A61N 5/1049* (2013.01); *A61N 5/1067* (2013.01); *A61N 5/1071* (2013.01); *A61N 5/1082* (2013.01); *A61N 2005/1085* (2013.01); *A61N 2005/1091* (2013.01); *A61N 2005/1095* (2013.01); *G06T 7/30* (2017.01); *G06T 11/008* (2013.01); *G06T 2207/10081* (2013.01); *G06T 2210/41* (2013.01); *G06T 2211/404* (2013.01); *G06T 2211/412* (2013.01); *G06T 2211/424* (2013.01); *G06T 2211/428* (2013.01); *G06T 2211/432* (2013.01)

(56) References Cited

U.S. PATENT DOCUMENTS

| | | |
|---|---|---|
| 6,233,478 B1 | 5/2001 | Liu |
| 6,307,909 B1 | 10/2001 | Flohr et al. |
| 7,050,528 B2 | 5/2006 | Chen |
| 7,336,759 B2 | 2/2008 | Nukui |
| 7,660,380 B2 | 2/2010 | Boese et al. |
| 8,116,430 B1 | 2/2012 | Shapiro et al. |
| 8,467,497 B2 | 6/2013 | Lu et al. |
| 8,588,363 B2 | 11/2013 | Flohr |
| 9,400,332 B2 | 7/2016 | Star-Lack et al. |
| 2003/0007601 A1 | 1/2003 | Jaffray et al. |
| 2003/0076927 A1 | 4/2003 | Shigeyuki et al. |
| 2004/0091079 A1 | 5/2004 | Zapalac |
| 2004/0202360 A1 | 10/2004 | Besson |
| 2005/0053188 A1 | 3/2005 | Gohno |
| 2005/0251029 A1 | 11/2005 | Khamene et al. |
| 2006/0109954 A1 | 5/2006 | Gohno |
| 2006/0262894 A1 | 11/2006 | Bernhadt et al. |
| 2007/0127621 A1 | 6/2007 | Grass et al. |
| 2007/0189444 A1 | 8/2007 | Van Steven-Daal et al. |
| 2008/0103834 A1* | 5/2008 | Reiner .............. A61B 6/5294 705/3 |
| 2008/0112532 A1 | 5/2008 | Schlomka et al. |
| 2009/0080603 A1 | 3/2009 | Shukla et al. |
| 2009/0135994 A1 | 5/2009 | Yu et al. |
| 2009/0161826 A1 | 6/2009 | Gertner et al. |
| 2009/0225932 A1 | 9/2009 | Zhu et al. |
| 2009/0283682 A1 | 11/2009 | Star-Lack et al. |
| 2009/0304142 A1 | 12/2009 | Ruimi et al. |
| 2010/0046819 A1 | 2/2010 | Noo et al. |
| 2010/0142791 A1 | 6/2010 | Tsuji |
| 2010/0208964 A1 | 8/2010 | Wiegert et al. |
| 2011/0142312 A1 | 6/2011 | Toth et al. |
| 2011/0255656 A1 | 10/2011 | Star-Lack et al. |
| 2012/0014582 A1 | 1/2012 | Schaefer et al. |
| 2012/0207370 A1 | 8/2012 | Fahimian et al. |
| 2012/0263360 A1 | 10/2012 | Zhu et al. |
| 2012/0294504 A1 | 11/2012 | Kyriakou |
| 2013/0101082 A1 | 4/2013 | Jordan et al. |
| 2013/0294570 A1 | 11/2013 | Hansis |
| 2014/0018671 A1 | 1/2014 | Li et al. |
| 2014/0086383 A1 | 3/2014 | Huwer et al. |
| 2014/0169652 A1* | 6/2014 | Vic ........................ G06T 7/344 382/131 |
| 2015/0297165 A1 | 10/2015 | Tanaka et al. |
| 2015/0305696 A1 | 10/2015 | Yamakawa et al. |
| 2016/0016009 A1 | 1/2016 | Manzke et al. |
| 2016/0120486 A1 | 5/2016 | Goto et al. |
| 2016/0220844 A1* | 8/2016 | Paysan ................... G16H 10/60 |
| 2016/0262709 A1 | 9/2016 | Siewerdsen et al. |
| 2017/0000428 A1 | 1/2017 | Goto |
| 2017/0197098 A1 | 7/2017 | Hirasawa et al. |
| 2017/0205360 A1 | 7/2017 | Cinquin et al. |
| 2017/0278277 A1 | 9/2017 | Morf et al. |
| 2017/0332982 A1 | 11/2017 | Koehler et al. |
| 2018/0028143 A1 | 2/2018 | Wiggers et al. |
| 2018/0070894 A1 | 3/2018 | Osaki et al. |
| 2018/0192978 A1 | 7/2018 | Naylor |
| 2018/0345042 A1 | 12/2018 | Voronenko et al. |
| 2019/0099149 A1 | 4/2019 | Li |
| 2020/0016432 A1 | 1/2020 | Maolinbay |
| 2020/0121267 A1 | 4/2020 | Deutschmann |
| 2020/0402644 A1* | 12/2020 | Zhou ...................... G16H 30/20 |
| 2021/0165122 A1 | 6/2021 | Morton |

FOREIGN PATENT DOCUMENTS

| | | |
|---|---|---|
| EP | 2383702 A1 | 11/2011 |
| JP | H09 218939 A | 8/1997 |
| JP | 2004 136021 | 5/2004 |
| JP | 2008 036275 | 2/2008 |
| WO | 2005/112753 A2 | 12/2005 |
| WO | 2006/078386 A2 | 7/2006 |
| WO | 2010/014288 A1 | 2/2010 |
| WO | 2010/099621 A1 | 9/2010 |
| WO | 2015/103184 A1 | 7/2015 |
| WO | 2018/156968 A1 | 8/2018 |
| WO | 2018/183748 A1 | 10/2018 |

OTHER PUBLICATIONS

Office Action from U.S. Appl. No. 16/694,190 dated Mar. 26, 2021 (9 pages).

Notice of Allowance from U.S. Appl. No. 16/694,190 dated Jun. 23, 2021 (8 pages).

Office Action from U.S. Appl. No. 16/694,230 dated Apr. 1, 2021 (6 pages).

Office Action from U.S. Appl. No. 16/694,202 dated Apr. 9, 2021 (12 pages).

Office Action from U.S. Appl. No. 16/694,192 dated Jun. 10, 2021 (10 pages).

Office Action from U.S. Appl. No. 16/694,218 dated Apr. 15, 2021 (7 pages).

(56) References Cited

OTHER PUBLICATIONS

Clackdoyle, R. and Desbat, L., "Data consistency conditions for truncated fanbeam and parallel projections." Med. Phys. 42 (2015), pp. 831-845.
Defrise, M., Noo, F. and Kudo, H., "A solution to the long-object problem in helical cone-beam tomography." Phys. Med. Biol. 45 (2000) pp. 623-643.
Noo et al., "A new scheme for view-dependent data differentiation in fan-beam and cone-beam computed tomography" Phys. Med. Biol. 52 (2007) pp. 5393-5414.
Hsieh, J., et al. "A novel reconstruction algorithm to extend the CT scan field-of-view." Med. Phys. 31(9), 2004, pp. 2385-2391.
Katsevich, A., "An improved exact filtered backprojection algorithm for spiral computed tomography." Advances in Applied Mathematics, 32(2004), pp. 681-697.
Kudo et al., "Exact and approximate algorithms for helical cone-beam CT", Phys. Med. Biol. 49(13), 2004, pp. 2913-2931.
Kunze, et al., "Cone beam reconstruction with displaced flat panel detector", 10th International Meeting on Fully Three-Dimensional Image Reconstruction in Radiology and Nuclear Medicine, 2009, pp. 138-141.
Li et al., "Scatter kernel estimation with an edge-spread function method for cone-beam computed tomography imaging," Phys. Med. Biol. 51 (2008) pp. 6729-6748.
Maslowski, et al. "Acuros CTS: A fast, linear Boltzmann transport equation solver for computed tomography scatter—Part I: Core algorithms and validation." Med. Phys. 45 (5), 2018, pp. 1899-1913.
Ning, et al., "X-ray scatter correction algorithm for cone beam CT imaging." Med. Phys. 31(5), 2004, pp. 1195-1202.
Schafer, et al., "FBP and BPF reconstruction methods for circular X-ray tomography with off-center detector", Med. Phys., 38(7), 2011, pp. S85-S94.
Schafer, et al., "Cone-beam filtered back-projection for circular X-ray tomography with off-center detector", 10th International Meeting on Fully Three-Dimensional Image Reconstruction in Radiology and Nuclear Medicine, 2009, pp. 86-89.
Siewerdsen, et al., "A simple, direct method for x-ray scatter estimation and correction in digital radiography and cone-beam CT." Med. Phys., 33(1), 2006, pp. 187-197.
Sun, et al. "Improved scatter correction using adaptive scatter kernel superposition." Phys. Med. Biol. 55(22), 2010, p. 6695-6720.
Tang, et al., "A sinogram extrapolation method for CT field of view extension." Proceedings of the Fifth CT Meeting, 2018, pp. 206-209.
Yu, L., et al., "Radiation dose reduction in computed tomography: techniques and future perspective." Imaging Med. 1 (1), 2009, pp. 65-84.
Zamyatin et al., "Helical cone beam CT with an asymmetrical detector," Med. Phys. 32 (10), 2005, pp. 3117-3127.
Zbijewski, W. et al. "Efficient Monte Carlo based scatter artifact reduction in cone-beam micro-CT." IEEE transactions on medical imaging, 25(7), 2006, pp. 817-827.
Zhu, et al. "Scatter correction method for X-ray CT using primary modulation: Theory and preliminary results." IEEE transactions on medical imaging, 25(12), 2006, pp. 1573-1587.
Restriction Requirement from U.S. Appl. No. 16/694,210 dated Jun. 10, 2021 (6 pages).
International Search Report and Written Opinion from PCT/US2019/063080 dated Mar. 16, 2020.

International Search Report and Written Opinion from PCT/US2019/063071 dated Mar. 18, 2020.
International Search Report and Written Opinion from PCT/US2019/063073 dated Apr. 3, 2020.
International Search Report and Written Opinion from PCT/US2019/063078 dated Oct. 8, 2020.
International Search Report and Written Opinion from PCT/US2019/063083 dated Mar. 16, 2020.
International Search Report and Written Opinion from PCT/US2019/063085 dated Mar. 16, 2020.
Invitation to Pay Additional Fees from PCT/US2019/063086 dated Mar. 26, 2020.
International Search Report and Written Opinion from PCT/US2019/063087 dated Apr. 3, 2020.
International Search Report and Written Opinion from PCT/US2019/063077 dated Mar. 16, 2020.
International Search Report and Written Opinion from PCT/US2019/063076 dated Mar. 16, 2020.
International Search Report and Written Opinion from PCT/US2019/063074 dated Mar. 23, 2020.
International Search Report and Written Opinion from PCT/US2019/063086 dated Nov. 16, 2020.
Kang et al., "Accurate for Head and Neck Cancer Patients Using 2D and 3D Image Guidance", Journal of Applied Clinical Medical Physics, vol. 12, No. 1, Dec. 1, 2011, pp. 86-96, XP055734549.
Ramamurthi et al., "Region of Interest Cone Beam Tomography With Prior CT Data," Conference Record of the 37th Asilomar Conference on Signals, Systems, & Computers, vol. 2, Nov. 9, 2003, pp. 1924-1927.
Spearman, et al. Effect of Automated Attenuation-Based Tube Voltage Selection on Radiation Dose at CT: An Observational Study on a Global Scale 11 , RADIOLOGY, vol. 279, No. Apr. 1, 2016 (Apr. 1, 2016), pp. 167-174, XP055734550.
Vinson et al., "X-Ray Micro-CT With a Displaced Detector Array: Application to Helical Cone-Beam Reconstruction," Medical Physics, vol. 30, No. 10, Oct. 1, 2003, pp. 2758-2761.
Wang et al., "A General Cone-Beam Reconstruction Algorithm," IEEE Transactions on Medical Imaging, vol. 12, No. 3, Sep. 1, 1993.
Wang, "X-Ray Micro-CT With a Displaced Detector Array," Medical Physics, vol. 29, No. 7, Jul. 1, 2002.
Office Action from U.S. Appl. No. 16/694,161 dated Sep. 13, 2021, 18 pages.
Anas, et al. High-quality 3D correction of ring and radiant artifacts in flat panel detector-based cone beam vol. CT Imaging, Phys. Med. Biol., 2011, pp. 6495-6519, vol. 56.
Bootsma, et al., Spatial frequency spectrum of the x-ray scatter distribution in CBCT projections, Med. Phys., Nov. 2013, p. 111901-1-111901-15, vol. 40, No. 11.
International Search Report and Written Opinion from PCT/US2021/039824 dated Mar. 4, 2022.
International Search Report and Written Opinion from PCT/US2021/042906 dated Mar. 21, 2022.
Rührnschopf, et al., A general framework and review of scatter correction methods in cone beam CT. Part 2: Scatter estimation approaches, Med. Phys. Sep. 2011, pp. 5186-5199, vol. 38, No. 9.
Yang, et al., Scattering estimation for cone-Beam CT Using Local Measurement Based on Compressed Sensing, IEEE transactions on Nuclear Science, Mar. 2018, pp. 941-949, vol. 65, No. 3.

* cited by examiner

OPTIMIZED SCANNING METHODS AND TOMOGRAPHY SYSTEM USING REGION OF INTEREST DATA

CROSS-REFERENCE TO RELATED APPLICATIONS

This application claims the benefit of eleven U.S. provisional patent applications, including Ser. No. 62/773,712, filed Nov. 30, 2018; Ser. No. 62/773,700, filed Nov. 30, 2018; Ser. No. 62/796,831, filed Jan. 25, 2019; Ser. No. 62/800,287, filed Feb. 1, 2019; Ser. No. 62/801,260, filed Feb. 5, 2019; Ser. No. 62/813,335, filed Mar. 4, 2019; Ser. No. 62/821,116, filed Mar. 20, 2019; Ser. No. 62/836,357, filed Apr. 19, 2019; Ser. No. 62/836,352, filed Apr. 19, 2019; Ser. No. 62/843,796, filed May 6, 2019; and Ser. No. 62/878,364, filed Jul. 25, 2019. This application is also related to ten non-provisional U.S. patent applications filed on the same day, including Ser. No. 16/694,145, filed Nov. 25, 2019, entitled "MULTIMODAL RADIATION APPARATUS AND METHODS;" Ser. No. 16/694,148, filed Nov. 25, 2019, entitled "APPARATUS AND METHODS FOR SCALABLE FIELD OF VIEW IMAGING USING A MULTI-SOURCE SYSTEM;" Ser. No. 16/694,161, filed Nov. 25, 2019, entitled "INTEGRATED HELICAL FAN-BEAM COMPUTED TOMOGRAPHY IN IMAGE-GUIDED RADIATION TREATMENT DEVICE;" Ser. No. 16/694,166, filed Nov. 25, 2019, entitled "COMPUTED TOMOGRAPHY SYSTEM AND METHOD FOR IMAGE IMPROVEMENT USING PRIOR IMAGE;" Ser. No. 16/694,190, filed Nov. 25, 2019, entitled "HELICAL CONE-BEAM COMPUTED TOMOGRAPHY IMAGING WITH AN OFF-CENTERED DETECTOR;" Ser. No. 16/694,192, filed Nov. 25, 2019, entitled ";" Ser. No. 16/694,202, filed Nov. 25, 2019, entitled "METHOD AND APPARATUS FOR SCATTER ESTIMATION IN CONE-BEAM COMPUTED TOMOGRAPHY;" Ser. No. 16/694,210, filed Nov. 25, 2019, entitled "ASYMMETRIC SCATTER FITTING FOR OPTIMAL PANEL READOUT IN CONE-BEAM COMPUTED TOMOGRAPHY;" Ser. No. 16/694,218, filed Nov. 25, 2019, entitled "METHOD AND APPARATUS FOR IMPROVING SCATTER ESTIMATION AND CORRECTION IN IMAGING;" and Ser. No. 16/694,230, filed Nov. 25, 2019, entitled "METHOD AND APPARATUS FOR IMAGE RECONSTRUCTION AND CORRECTION USING INTER-FRACTIONAL INFORMATION." The contents of all above-identified patent application(s) and patent(s) are fully incorporated herein by reference.

FIELD OF THE INVENTION

Aspects of the disclosed technology relate to computed tomography (CT) imaging, and, more particularly, to a system and method for optimization of computed tomography CT and image-guided radiation treatment (IGRT) using data related to a region of intent (ROI).

BACKGROUND

Computed tomography (CT) imaging generally involves exposing a patient or a portion of a patient to a radiation source and positioning a radiation detector to receive x-ray radiation from the radiation source. The radiation source and detector are moved to a variety of positions around the patient, and the received radiation is used to generate an image of the patient.

Radiotherapy is one area where CT imaging is being employed with greater frequency. Radiotherapy is often carried out by directing a high-energy beam of x-rays (e.g., at an energy level in the megavoltage range) toward a tumor or other region of interest within a patient. The goal of the treatment is to focus the high-energy x-ray beam on the region of interest, while minimizing the exposure of surrounding tissue. So-called image-guided radiation treatment (IGRT) can make use of CT imaging to collect images of a patient for use in image-based pre-delivery steps, which can include treatment planning. CT Image acquisition can also be used to confirm that therapeutic radiation beams are correctly directed to and treating the region of interest.

BRIEF SUMMARY

In one embodiment, an imaging method for use with IGRT of a patient includes receiving image data corresponding to a prior image of the patient, where the image data includes data corresponding to a region of interest, obtaining projection image data of the patient, performing an image reconstruction based on the obtained projection image data of the patient to obtain a patient image, registering the prior image with the obtained patient image to obtain a registered image, identifying the ROI in the registered image, projecting ROI image data based on the prior image, generating an optimized set of parameters using the projected ROI image data, and performing a CT scan of the patient using said optimized set of parameters.

Features that are described and/or illustrated with respect to one embodiment may be used in the same way or in a similar way in one or more other embodiments and/or in combination with or instead of the features of the other embodiments.

The descriptions of the invention do not limit the words used in the claims in any way or the scope of the claims or invention. The words used in the claims have all of their full ordinary meanings.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify embodiments of this invention. It will be appreciated that illustrated element boundaries (e.g., boxes, groups of boxes, or other shapes) in the figures represent one embodiment of boundaries. In some embodiments, one element may be designed as multiple elements or that multiple elements may be designed as one element. In some embodiments, an element shown as an internal component of another element may be implemented as an external component and vice versa. Furthermore, elements may not be drawn to scale.

Figure 1:
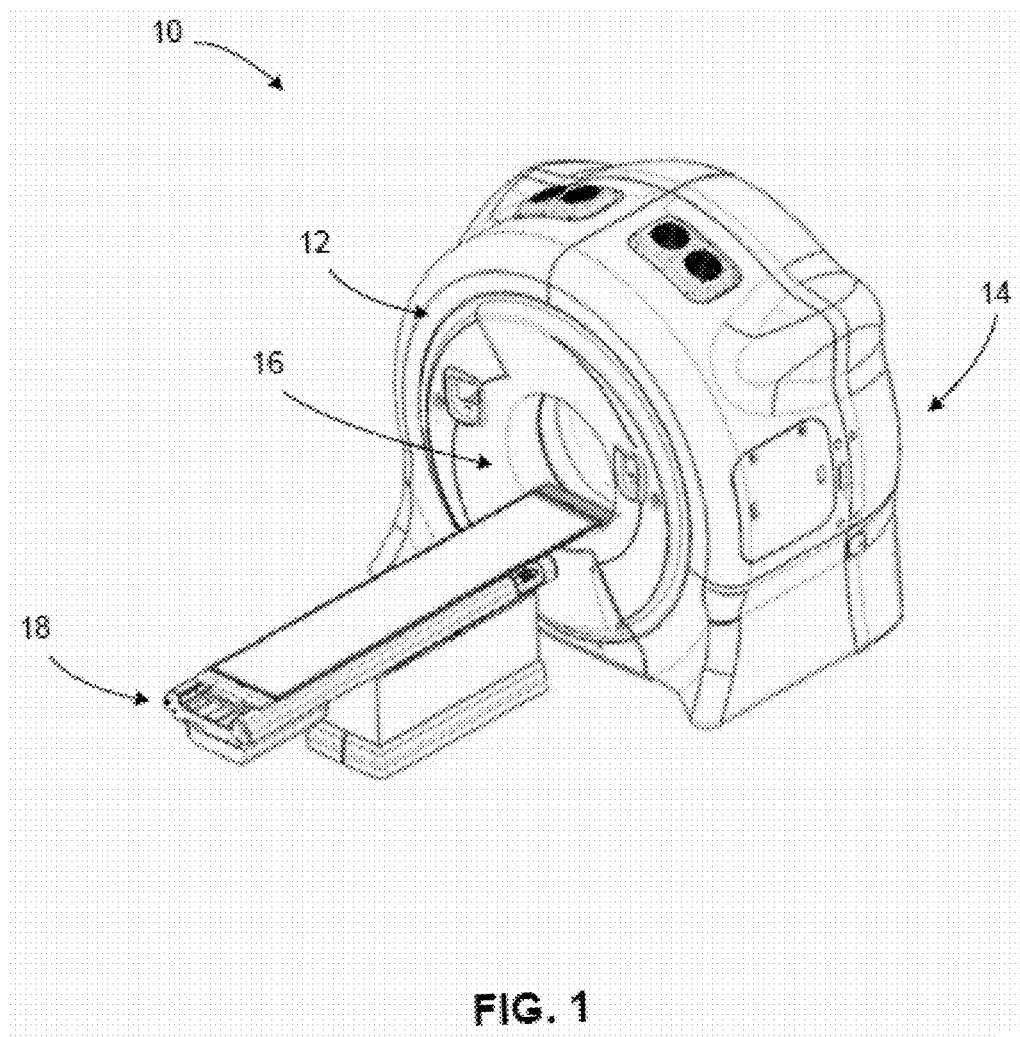
FIG. 1 is a perspective view of a radiotherapy delivery device in accordance with one aspect of the disclosed technology.

It should be noted that all the drawings are diagrammatic and not drawn to scale. Relative dimensions and proportions of parts of these figures have been shown exaggerated or reduced in size for the sake of clarity and convenience in the drawings. The same reference numbers are generally used to refer to corresponding or similar features in the different embodiments. Accordingly, the drawing(s) and description are to be regarded as illustrative in nature and not as restrictive.

DETAILED DESCRIPTION

The following includes definitions of exemplary terms that may be used throughout the disclosure. Both singular and plural forms of all terms fall within each meaning.

"Component," as used herein can be defined as a portion of hardware, a portion of software, or a combination thereof. A portion of hardware can include at least a processor and a portion of memory, wherein the memory includes an instruction to execute. A component may be associated with a device.

"Logic," synonymous with "circuit" as used herein, includes but is not limited to hardware, firmware, software and/or combinations of each to perform a function(s) or an action(s). For example, based on a desired application or needs, logic may include a software-controlled microprocessor, discrete logic such as an application specific integrated circuit (ASIC), or other programmed logic device and/or controller. Logic may also be fully embodied as software.

"Processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read-only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

"Signal," as used herein includes, but is not limited to, one or more electrical signals, including analog or digital signals, one or more computer instructions, a bit or bit stream, or the like.

"Software", as used herein, includes but is not limited to one or more computer readable and/or executable instructions that cause a computer, processor, logic, and/or other electronic device to perform functions, actions, and/or behave in a desired manner. The instructions may be embodied in various forms such as routines, algorithms, modules, or programs including separate applications or code from dynamically linked sources or libraries.

As is discussed in more detail below, aspects of the disclosed technology relate to CT imaging systems and methods, or a radiotherapy delivery device, and method that allows for controlling exposure of a beam from a source of imaging radiation of the radiation delivery device based on one or more parameters of a region of interest of a patient. As a result, targeted and/or reduced radiation exposure of the patient or region of interest of the patient may be better achieved.

Where radiotherapy is intended, the disclosed technology may make use of integrated kilovoltage (kV) CT for use in conjunction with or as part of IGRT.

In accordance with one implementation, the image acquisition methodology includes or otherwise makes use of a helical source trajectory (e.g., a continuous source rotation about a central axis together with longitudinal movement of a patient support through a gantry bore) with a fan or "thick-fan" kV beam collimation, together with fast slip ring rotation, to provide kV CT imaging on a radiation therapy delivery platform. It will be appreciated that such an implementation can provide reduced scatter and improved scatter estimation to enable kV images of higher quality than conventional systems.

In accordance with another implementation, the image acquisition methodology includes or otherwise makes use of an axial scan with the patient being moved between consecutive scans or gantry movements.

The present disclosure recognizes benefits associated with a radiation delivery device and method using region of interest (ROI) guidance for controlling exposure of a beam from a source of imaging radiation of the radiation delivery device based on one or more parameters or characteristics of a ROI of a patient. Such benefits may include, but are not limited to, reduced scan time for imaging of anatomical context regions, reduced x-ray scatter for improved image quality, radiation dose optimization including targeted dosing relative to a ROI and/or reduced radiation exposure to the patient or ROI of the patient. Another benefit may be a more uniform exposure of a targeted portion of the ROI to radiation at each of a plurality of view angles about the targeted portion, better accounting for variations in attenuation of the radiation at the plurality of view angles, and thus better utilizing the limited dynamic range of the flat panel detector for improved image quality. The disclosed technology may be employed in kV CT imaging or kV CT imaging associated with IGRT, such as for patient positioning, motion tracking, or beam tracking for an imaging radiation source or a therapeutic radiation source. These benefits may be realized through the use of a prior image that is then registered with the patient positioned on the patient support for a CT scan and/or IGRT treatment.

While aspects of the disclosed technology will be described in connection with the prior or previously-acquired image being a prior planning image (e.g., an image acquired before treatment for the purposes of generating a treatment plan for use in connection with an IGRT procedure), it will be appreciated that aspects of the disclosed technology can be carried out in a general imaging environment (e.g., in a standard CT imaging environment separate from any IGRT application).

For example, in some embodiments, the disclosed technology relates to a CT system separate from a radiotherapy system. In other embodiments, a radiotherapy delivery device and method can make use of an integrated low-energy radiation source for CT for use in conjunction with or as part of IGRT. In particular, for example, the radiotherapy delivery device and method can combine a low-energy radiation source for imaging in a gantry with a high-energy radiation source for therapeutic treatment. In one embodiment, the low-energy radiation source is a kilovolt (kV) radiation source as part of a CT system and the high-energy radiation source for therapeutic treatment is a megavolt (MV) radiation source. Embodiments below mentioning kV radiation sources may also utilize other low-energy radiation sources.

As mentioned above, the image acquisition system need not be associated with an IGRT system with a dedicated kV imaging source. For example, the involved image acquisition system may include a MV x-ray tube and MV x-ray detector, a kV x-ray tube and a kV x-ray detector, or combinations of both. As discussed in more detail below, these imaging sources and detectors may be mounted in various combinations on a CT-like gantry (e.g., with a slip-ring), on a robotic arm, on two robotic arms, and/or on other mounting devices.

In accordance with one embodiment, the method can be carried out on the system shown in FIG. 1 and FIG. 2 and described below. However, it will be appreciated that the imaging method can be carried out on a different computed tomography imaging system (e.g., a MV CT system and/or a kV CT system, where the source and/or the detector are operatively coupled to one or more robotic arms, such as a C-arm system) without departing from the scope of the disclosed technology.

Figure 2:
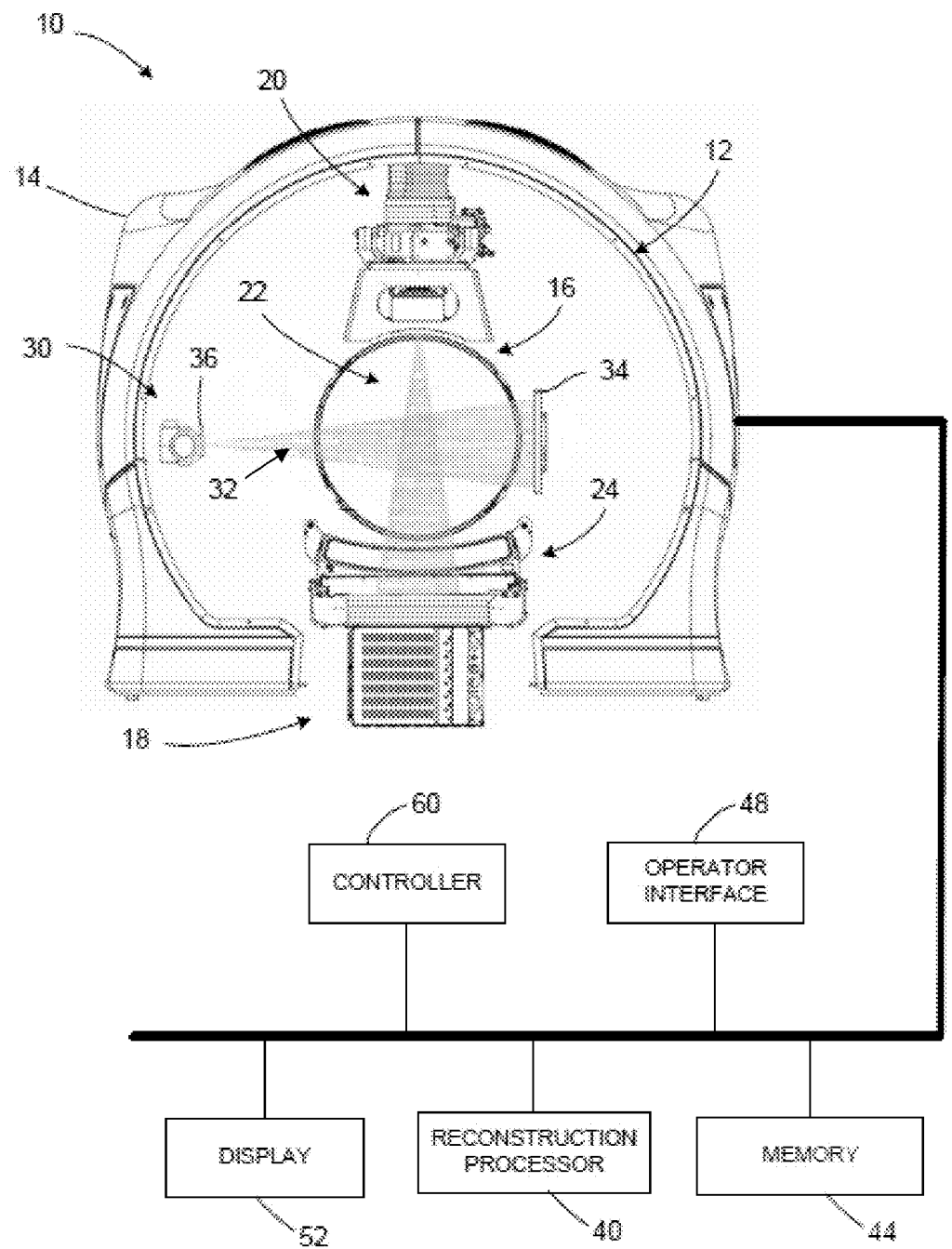
FIG. 2 is a diagrammatic illustration of a radiotherapy delivery device in accordance with one aspect of the disclosed technology.

With reference to FIG. 1 and FIG. 2, a radiotherapy device 10 is provided. It will be appreciated that the radiotherapy device 10 can be used for a variety of applications, including, but not limited to, image-guided radiation treatment or therapy (IGRT). The radiotherapy device 10 can be used to carry out the imaging methods described more fully below. The radiotherapy device 10 includes a rotatable gantry system, referred to as gantry 12 supported by or otherwise housed in a support unit or housing 14. Gantry herein refers to a gantry system that comprises one or more gantries (e.g., ring or C-arm) capable of supporting one or more radiation sources and/or associated detectors as they rotate around a target. For example, in one embodiment, a first radiation source and its associated detector may be mounted to a first gantry of the gantry system and a second radiation source and its associated detector may be mounted to a second gantry of the gantry system. In another embodiment, more than one radiation source and associated detector(s) may be mounted to the same gantry of the gantry system, including, for example, where the gantry system is comprised of only one gantry. Various combinations of gantries, radiation sources, and radiation detectors may be combined into a variety of gantry system configurations to image and/or treat the same volume within the same apparatus. For example, kV and MV radiation sources can be mounted on the same or different gantries of the gantry system and selectively used for imaging and/or treatment as part of an IGRT system. If mounted to different gantries, the radiation sources are able to rotate independently, but are still able to simultaneously image the same (or nearly the same) volume. A rotatable ring gantry 12 may be capable of 10 revolutions per minute (rpm) or more (e.g., using fast slip ring rotation, including, e.g., up to 10 rpm, up to 20 rpm, up to 60 rpm, or more rpm). The rotatable gantry 12 defines a gantry bore 16 into and through which a patient can be moved and positioned for imaging and/or treatment. In accordance with one embodiment the rotatable gantry 12 is configured as a slip ring gantry to provide continuous rotation of an imaging radiation source and an associated radiation detector while providing sufficient bandwidth for the imaging data received by the detector. A slip-ring gantry can eliminate gantry rotations in alternating directions in order to wind and unwind cables carrying the power and signals associated with the device. As is discussed more fully below, such a configuration can allow for continuous helical (e.g., fan-beam, cone-beam, etc.) computed tomography, even when integrated into an IGRT system.

A patient support 18 is positioned adjacent to the rotatable gantry 12 and configured to support a patient, typically in a horizontal position, for longitudinal movement into and within the rotatable gantry 12. The patient support 18 can move the patient, for example, in a direction perpendicular to the plane of rotation of the gantry 12 (along or parallel to the rotation axis of the gantry 12). The patient support 18 can be operatively coupled to a patient support controller for controlling movement of the patient and patient support 18. The patient support controller can be synchronized with the rotatable gantry 12 and sources of radiation mounted to the rotating gantry for rotation about a patient longitudinal axis in accordance with a commanded imaging and/or treatment plan. In some embodiments, the patient support can also be moved in a limited range up and down, left and right once it is in the bore 16 to adjust the patient position for optimal treatment. It will be appreciated that other variations can be employed without departing from the scope of the disclosed technology. For example, the rotatable gantry 12 and patient support can be controlled such that the gantry 12 rotates in a "back-and-forth" manner (e.g., alternating clockwise rotation and counterclockwise rotation) around a patient supported on the patient support (as opposed to continuously, as is described above) as the support is controlled to move (at a constant or variable speed) relative to the rotatable gantry 12. In another embodiment, with successive step-and-shoot circular scans, movement of the patient support 18 in the longitudinal direction (step) alternates with a scanning revolution by the rotatable gantry 12 (shoot) until the desired volume is captured. The device 10 is capable of volume-based and planar-based imaging acquisitions. For example, in various embodiments, the device 10 may be used to acquire volume images and/or planar images and execute the associated processing methods described below.

Various other types of radiation source and/or patient support movement may be utilized to achieve relative motion of the radiation source and the patient for generation of projection data. Non-continuous motion of the radiation source and/or patient support, continuous but variable/non-constant (including linear and non-linear) linear movement, speed, and/or trajectories, etc., and combinations thereof may be used, including in combination with the various embodiments of radiotherapy devices 10 described above. The scan speed of a patient on the support can be varied based on either how fast the gantry rotates or the speed at which the patient support moves in and out of the gantry.

As shown in FIG. 2, the radiotherapy device 10 includes a first source of radiation 20 coupled to or otherwise supported by the rotatable gantry 12. In accordance with one embodiment, the first source of radiation 20 is configured as a source of therapeutic radiation, such as a high-energy source of radiation used for treatment of a tumor within a patient in a ROI. It will be appreciated that the source of therapeutic radiation can be a high-energy x-ray beam (e.g., megavoltage (MV) x-ray beam), and/or a high-energy particle beam (e.g., a beam of electrons, a beam of protons, or a beam of heavier ions, such as carbon) or another suitable form of high-energy radiation without departing from the scope of the disclosed technology. In one embodiment, the first source of radiation 20 comprises a mega-electron volt peak photon energy (MeV) of 1 MeV or greater. In one embodiment, the high-energy x-ray beam has an average energy greater than 0.8 MeV. In another embodiment, the high-energy x-ray beam has an average energy greater than 0.2 MeV. In another embodiment, the high-energy x-ray beam has an average energy greater than 150 keV. Generally, the first source of radiation 20 has a higher energy level (peak and/or average, etc.) than the second source of radiation 30.

The imaging system, described in detail below, comprises a second source of radiation 30, which may be an independent x-ray imaging source producing relatively low intensity and lower energy imaging radiation. In one embodiment, the second source of radiation 30 is an x-ray source, configured as a kilovoltage (kV) source (e.g., a clinical x-ray source having an energy level in the range of about 20 kV to about 150 kV). In one embodiment, the kV source of radiation comprises a kilo-electron volt peak photon energy (keV) up to 150 keV. The imaging radiation source can be any type of transmission source suitable for imaging. For example, the imaging radiation source may be, for example, an x-ray generating source (including for CT) or any other way to produce photons with sufficient energy and flux (such as, e.g., a gamma-source (e.g., Cobalt-57, energy peak at 122 keV), an x-ray fluorescence source (such as fluorescence source through Pb k lines, two peaks @about 70 keV and @about 82 keV), etc.). References herein to x-ray, x-ray imaging, x-ray imaging source, etc. are exemplary for particular embodiments. Other imaging transmission sources can be used interchangeably in various other embodiments.

It will be further appreciated that the first source of radiation 20 can emit one or more beams of radiation (indicated generally by 22) toward a region-of-interest (ROI) within a patient supported on the patient support 18. The first source of radiation can emit one or more beams of radiation in accordance with a treatment plan. It also will be appreciated that the treatment plan can include detailed parameters regarding source angular position, beam geometry, beam intensity, modulation, exposure, and the like. It will be further be appreciated that additionally or alternatively, such parameters, also herein referred to as scan parameters or imaging parameters, can be automatically calculated and or selectively adjusted relative to one or more parameters of at least a portion of the ROI in accordance with the disclosed technology, detailed below.

In one embodiment, the first source of radiation 20 is a LINAC producing therapeutic radiation (e.g., MV) and the imaging system comprises an independent second source of radiation 30 producing relatively low intensity and lower energy imaging radiation (e.g., kV). In other embodiments, the first source of radiation 20 could be a radioisotope, such as, for example, Co-60, which can generally have energy>1 MeV. The first source of radiation 20 can emit one or more beams of radiation (indicated generally by 22) toward a region-of-interest (ROI) within a patient supported on the patient support 18 in accordance with a treatment plan.

As discussed in detail below, sources of radiation 20, 30 may be used in conjunction with one another to provide higher quality and better utilized images. In other embodiments, at least one additional radiation source can be coupled to the rotatable gantry 12 and operated to acquire projection data at a peak photon energy distinct from the peak photon energies of sources of radiation 20, 30.

Although FIGS. 1 and 2 depict a radiotherapy device 10 with a radiation source 20 mounted to a ring gantry 12, other embodiments may include other types of rotatable imaging apparatuses, including, for example, C-arm gantries and robotic arm-based systems. In gantry-based systems, a gantry rotates the imaging radiation source 30 around an axis passing through the isocenter. Gantry-based systems include C-arm gantries, in which the imaging radiation source 30 is mounted, in a cantilever-like manner, over and rotates about the axis passing through the isocenter. Gantry-based systems further include ring gantries, for example, rotatable gantry 12, having generally toroidal shapes in which the patient's body extends through a bore of the ring/toroid, and the imaging radiation source 30 is mounted on the perimeter of the ring and rotates about the axis passing through the isocenter. In some embodiments, the gantry 12 rotates continuously. In other embodiments, the gantry 12 utilizes a cable-based system that rotates and reverses repeatedly.

First detector 24 can be coupled to or otherwise supported by the rotatable gantry 12 and positioned to receive radiation 22 from the first source of radiation 20. The first detector 24 can detect or otherwise measure the amount of radiation not attenuated and therefore infer what was in fact attenuated by the patient or associated patient ROI (by comparison to what was initially generated). The first detector 24 can detect or otherwise collect attenuation data from different angles as the first radiation source 20 rotates around and emits radiation toward the patient. The collected attenuation data can be processed and reconstructed into one or more images of the patient's body.

The imaging system integrated within the radiotherapy device 10 can provide current images that are used to set up (e.g., align and/or register), plan, and/or guide the radiation delivery procedure (treatment). Typical set-up is accomplished by comparing current (in-treatment) images to pre-treatment image information (e.g., prior or otherwise previously-acquired image information). Pre-treatment image information may comprise, for example, CT data, CBCT data, magnetic resonance imaging (MRI) data, positron emission tomography (PET) data or 3D rotational angiography (3DRA) data, and/or any information obtained from these or other imaging modalities. In some embodiments, the imaging system can track in-treatment patient, target, or ROI motion.

Conventional in-treatment images typically comprise CBCT or two-dimensional images (typically x-ray). X-rays can be acquired at one or more different points of view (e.g., stereoscopic x-ray images), which can be compared with two-dimensional digitally reconstructed radiographs (DRRs) derived from the three-dimensional pre-treatment image information. CBCT can directly construct a 3D volumetric image from 2D projections of the target volume. As is known in the art, in one embodiment, CBCT has the ability to form a 3D image volume from a single gantry rotation about the target volume with a more isotropic spatial resolution. In other embodiments, CBCT can utilize helical scan trajectories.

As shown in FIG. 2, the imaging system integrated within the radiotherapy device 10 includes a second source of radiation 30 coupled to or otherwise supported by the rotatable gantry 12. As discussed above, the second source of radiation 30 can be configured as a source of imaging radiation (e.g., kV) for high-quality in-treatment images (indicated generally as 32) having an energy level less than the first source 20 of therapeutic radiation.

A second detector 34 (e.g., two-dimensional flat detector or curved detector) can be coupled to or otherwise supported by the rotatable gantry 12. The second detector 34 is positioned to receive radiation from the second source of radiation 30. The detector 34 can detect or otherwise measure the amount of radiation not attenuated and therefore infer what was in fact attenuated by the patient or associated patient ROI (by comparison to what was initially generated). The detector 34 can detect or otherwise collect attenuation data from different angles as the second radiation source 30 rotates around and emits radiation toward the patient.

A collimator or beamformer assembly (indicated generally as 36) is positioned relative to the second source of radiation 30 to selectively control and adjust a shape of a radiation beam 32 emitted by the second radiation source 30 to selectively expose a portion or region of the active area of the second radiation detector 34. The collimator 36 can also control how the radiation beam 32 is positioned on the detector 34. In one embodiment, the collimator 36 can have one degree/dimension of motion (e.g., to make a thinner or fatter slit). In another embodiment, the collimator 36 could have two degrees/dimensions of motion (e.g., to make various sized rectangles). In other embodiments, the collimator 36 may be capable of various other dynamically-controlled shapes, including, for example, parallelograms. All of these shapes may be dynamically adjusted during a scan. In some embodiments, blocking portions of the collimator can be rotated and/or translated.

The collimator/beamformer 36 may be configured in a variety of ways that allow it to adjust the shape of the radiation beam 32 emitted by the second source of radiation 30. For example, the collimator 36 can be configured to include a set of jaws or other suitable members that define and selectively adjust the size of an aperture through which the radiation beam from the second source of radiation 30 may pass in a collimated manner. In accordance with one exemplary configuration, the collimator 36 can include an upper jaw and a lower jaw, where the upper and lower jaws are movable in different directions (e.g., parallel directions) to adjust the size of the aperture through which the radiation beam from the second source of radiation 30 passes, and also to adjust the beam 32 position relative to the patient to illuminate only the portion of the patient to be imaged for optimized imaging and minimized patient dose. For example, a collimator can be configured as a multi-leaf collimator (MLC), which can include a plurality of interlaced leaves operable to move to one or more positions between a minimally-open or closed position and a maximally-open position. It will be appreciated that the leaves can be moved into desired positions to achieve a desired shape of a radiation beam being emitted by the radiation source. In one embodiment, the MLC is capable of sub-millimeter targeting precision.

In accordance with one embodiment, the shape of the radiation beam 32 from the second source of radiation 30 can be changed during an image acquisition. Stated differently, in accordance with one exemplary implementation, the collimator 36 leaf positions and/or aperture width can be adjusted before or during a scan. For example, in accordance with one embodiment, the collimator 36 can be selectively controlled and dynamically adjusted during rotation of the second source of radiation 30 such that the radiation beam 32 has a shape with sufficient primary/shadow regions and is adjusted to include only an object of interest during imaging (e.g., the prostate). The shape of the radiation beam 32 being emitted by the second source of radiation 30 can be selectively controlled during or after a scan, depending on the desired image acquisition, which may be based on imaging and/or therapeutic feedback, as discussed in more detail below.

It will be further appreciated that the first source of radiation 20 can include or otherwise be associated with a beamformer or collimator. The collimator/beamformer associated with the first source of radiation 20 can be configured in a number of ways, similar to the collimator 36 associated with the second source of radiation 30.

The collimator assembly 36 can be controlled to adjust the shape of the radiation beam 32 emitted by the second source of radiation 30 in a number of geometries, including, but not limited to, a fan beam, thick fan beam, or cone beam having a beam thickness (width) as low as one detector row width or including multiple detector rows, which may be only a portion of the detector's active area. In various embodiments, the thickness of the beam may expose several centimeters of a larger detector active area. For example, 3-4 centimeters (measured in the longitudinal direction in the detector plane) of a 5-6-centimeter detector may be selectively exposed to the imaging radiation 32. However, various other exposed and active area sizes or ratios of exposed-to-active detector area may be suitable in other embodiments.

In accordance with one exemplary embodiment, the radiotherapy device 10 has been described above as including a first source of radiation 20, a second source of radiation 30, a first radiation detector 24 positioned to receive radiation from the first source of radiation 20 and a second radiation detector 34 positioned to receive radiation from the second radiation source 30. It will be appreciated, however, that the radiotherapy device 10 can include a first source of radiation 20 (e.g., a source of therapeutic radiation), a second source of radiation 30 (e.g., a kV radiation source) and only a radiation detector 34 positioned to receive radiation from the second source of radiation 30 without departing from the scope of the disclosed technology.

The radiation source 20 may be mounted, configured, and/or moved into the same plane or a different plane (offset) than the radiation source 30. In some embodiments, scatter caused by simultaneous activation of the radiation sources 20, 30 may be incrementally reduced by offsetting the radiation planes. In other embodiments, scatter can be avoided by interleaving the activations. For example, with simultaneous multimodal imaging, the acquisitions can be concurrent, without having concurrent individual pulses. In another embodiment, use of shadow-based scatter correction can be used, for example, to address the problem of MV scatter on a kV detector.

Integrated as a radiotherapy device, apparatus 10 can provide images that are used to set up (e.g., align and/or register), plan, and/or guide a radiation delivery procedure (treatment). Typical set-up is accomplished by comparing current (in-treatment) images to pre-treatment image information. Pre-treatment image information may comprise, for example, CT data, CBCT data, MRI data, PET data or 3D rotational angiography (3DRA) data, and/or any information obtained from these or other imaging modalities. In some embodiments, the device 10 can track in-treatment patient, target, or ROI motion.

A reconstruction processor 40 can be operatively coupled to the first detector 24 and/or second detector 34. In one embodiment, the reconstruction processor 40 is configured to generate patient images based on radiation received by detectors 24, 34 from the radiation sources 20, 30. The reconstruction processor 40 may comprise a processor, memory, software, logic or other components and can implement one or more routines or steps to utilize scanning data and parameters to create patient images. It will be appreciated that the reconstruction processor 40 can be configured to be used to carry out the methods described more fully below. The apparatus 10 can also include a memory 44 suitable for storing information, including, but not limited to, processing and reconstruction algorithms and software, imaging parameters, image data from a prior or otherwise previously-acquired image (e.g., a planning image), treatment plans, and the like.

The radiotherapy device 10 can include an operator/user interface 48, where an operator of the radiotherapy device 10 can interact with or otherwise control the radiotherapy device 10 to provide input relating to scan or imaging parameters and the like. The operator interface 48 can include any suitable input devices, such as a keyboard, mouse, voice-activated controller, or the like. The radiotherapy device 10 can also include a display 52 or other human-readable element to provide output to the operator of the radiotherapy device 10. For example, the display 52 can allow the operator to observe reconstructed patient images and other information, such as imaging or scan parameters, related to operation of the radiotherapy device 10.

It will be appreciated that the collimator assembly 36 positioned relative to the second source of radiation 30 can be configured to provide dynamic collimation of a radiation beam being emitted by the second radiation source 30

The collimator assembly 36 can be controlled such that the beam 32 from the second radiation source 30 covers as much or as little of the second detector 34 based on the particular imaging task being carried out. For example, the collimator 36 can be selectively controlled to provide a fan beam having a fan thickness from a single detector row, which could be sub-millimeter, up to several centimeters, including, for example, a beam thickness of 3-4 centimeters (measured in the longitudinal direction in the detector plane). Such a beam configuration can be used in a continuous, helical fan-beam imaging mode in accordance with aspects of the disclosed technology. In other embodiments, circular imaging modes may be used, including with a larger fan beam or cone beam thickness. For example, for any mode, the collimator 36 can be selectively controlled to provide a beam having a thickness of about one centimeter. In accordance with another exemplary embodiment, the collimator 36 can be selectively controlled to provide a beam having a thickness of more than one centimeter or several centimeters, including, for example, between about two centimeters and about four centimeters. In accordance with another exemplary embodiment, the collimator 36 can be selectively controlled to provide a beam 32 having a thickness between about fifteen centimeters and about thirty centimeters. In accordance with another exemplary embodiment, the collimator 36 can be selectively controlled to provide a beam 32 having a thickness between about thirty-five centimeters and about forty centimeters. Generally, the system and beam geometry can be controlled to yield beams that are thin (e.g., single row), thick (e.g., multi-row), or cone-shaped.

In accordance with one implementation, the geometry of the beam 32 from the second radiation source 30 can be changed during an image acquisition. Stated differently, in accordance with one exemplary implementation, the collimator 36 leaf positions and/or aperture width can be adjusted before or during a scan. For example, in accordance with one embodiment, the collimator 36 can be selectively controlled and dynamically adjusted during rotation of the second radiation source 30 such that the beam 32 has a rectangular geometry that includes only an object of interest during imaging (e.g., the prostate).

As shown in FIG. 2, the radiotherapy device 10 includes a controller (indicated generally as 60) operatively coupled to one or more components of the radiotherapy system 10. The controller 60 controls the overall functioning and operation of the radiotherapy device 10, including providing power and timing signals to the first radiation source 20 and/or the second radiation source 30 and a gantry motor controller that controls rotational speed and position of the rotatable gantry 12. It will be appreciated that the controller 60 can encompass one or more of the following: a patient support controller, a gantry controller, a controller coupled to the first radiation source 20 and/or the second radiation source 30, a collimator assembly controller, a controller coupled to the first detector 24 and/or the second detector 34, and the like. In one embodiment controller 60 is a system controller that can control other components, devices, and/or controllers.

In various embodiments, the reconstruction processor 40, the operator interface 48, the display 52, the controller 60 and/or other components may be combined into one or more components or devices.

The radiotherapy system 10 may include various components, logic, and software. In one embodiment, the controller 60 comprises a processor, a memory, and software. By way of example and not limitation, a radiotherapy system (such as, for example, radiotherapy system 10 shown in FIGS. 1 and 2) can include various other devices and components (e.g., gantries, radiation sources, collimators, detectors, controllers, power sources, patient supports, among others) that can implement one or more routines or steps related to imaging and/or IGRT for a specific application, wherein a routine can include imaging, image-based pre-delivery steps, and/or treatment delivery, including respective device settings, configurations, and/or positions (e.g., paths/trajectories) which may be stored in memory. Other routines include processes and/or algorithms associated with data and image processing, including, for example, the processes described below. Furthermore, the controller(s) can directly or indirectly control one or more devices and/or components in accordance with one or more routines or processes stored in memory. An example of direct control is the setting of various radiation source or collimator parameters (power, speed, position, timing, modulation, etc.) associated with imaging or treatment. An example of indirect control is the communication of position, path, speed, etc. to a patient support controller or other peripheral device. The hierarchy of the various controllers that may be associated with a radiotherapy device 10 can be arranged in any suitable manner to communicate the appropriate commands and/or information to the desired devices and components.

Moreover, those skilled in the art will appreciate that the systems and methods may be implemented with other computer system configurations. The illustrated aspects of the invention may be practiced in distributed computing environments where certain tasks are performed by local or remote processing devices that are linked through a communications network. For example, in one embodiment, the reconstruction processor 40 may be associated with a separate system. In a distributed computing environment, program modules may be located in both local and remote memory storage devices. For instance, a remote database, a local database, a cloud-computing platform, a cloud database, or a combination thereof can be utilized with radiotherapy device 10.

Radiotherapy device 10 can utilize an exemplary environment for implementing various aspects of the invention including a computer, wherein the computer includes the controller 60 (e.g., including a processor and a memory, which may be memory 44) and a system bus. The system bus can couple system components including, but not limited to the memory to the processor, and can communicate with other systems, controllers, components, devices, and processors. Memory can include read only memory (ROM), random access memory (RAM), hard drives, flash drives, and any other form of computer readable media. Memory can store various software and data, including routines and parameters, which may comprise, for example, a treatment plan.

The first source of radiation 20 and/or second source of radiation 30 can be operatively coupled to a controller 60 configured to control the relative operation of the first source of radiation 20 and the second source of radiation 30. For example, the second source of radiation 30 can be controlled and operated simultaneously with the first source of the radiation 20. In addition, or alternatively, the second source of radiation 30 can be controlled and operated sequentially with the first source of radiation 20, depending on the particular treatment and imaging plan being implemented.

It will be appreciated that the second detector 34 can take on a number of configurations without departing from the scope of the disclosed technology. As illustrated in FIG. 2, the second detector 34 can be configured as a flat-panel detector (e.g., a multi-row flat panel detector). In accordance with another exemplary embodiment, the second detector 34 can be configured as a curved detector.

In the illustrated embodiment, the second source of radiation 30 and the associated second detector 34 are positioned approximately 180 degrees from one another about the rotating gantry. It will be appreciated that the second source of radiation 30 and the associated second detector 34 can be positioned in different orientations other than 180 degrees offset. For example, the second radiation source and the associated second detector can be positioned relative to one another to achieve a half-fan CT acquisition. In another exemplary embodiment second detector need not be directly 180 degrees from second radiation 30 source as shown in FIG. 2 but can be offset to either side of the location shown.

Regardless of the configuration or geometry of the second detector 34, it will be appreciated that the collimator assembly 36 positioned relative to or otherwise associated with the second source of radiation 30 can be selectively controlled to control the shape of the radiation beam 32 emitted by the second radiation source 30 to selectively expose part or all of the second radiation detector 34. For example, in accordance with one exemplary embodiment, the beam from the second source of radiation can be collimated or otherwise controlled to provide a fan or cone beam of imaging radiation. It will be appreciated that the size and geometry of the beam can be controlled based on the particular desired imaging application. In accordance with one example of the disclosed technology, the collimator assembly 36 can be selectively controlled such that the radiation beam 32 emitted by the second source of radiation is a fan beam, having a fan beam thickness greater than and down to about one centimeter. As discussed above, the geometry of the radiation beam 32 being emitted by the second radiation source can be changed during or after a scan, depending on the desired image acquisition, which may be based on imaging and/or therapeutic feedback.

It will be appreciated that the second source of radiation 30 and the second detector 34 positioned to receive radiation from the second source of radiation 30 can be configured to provide continuous rotation around the patient during an imaging scan. Further, synchronizing the motion and exposure of the second radiation source 30 with the longitudinal motion of the patient support can provide a continuous helical fan beam acquisition of a patient image during a procedure.

The following flow charts and block diagrams illustrate exemplary configurations and methodologies associated with CT and/or IGRT in accordance with the systems described above. The exemplary methodologies may be carried out in logic, software, hardware, or combinations thereof which may be comprised as parts of controller 60. In addition, although the procedures and methods are presented in an order, the blocks may be performed in different orders, including series and/or parallel. In particular, for example, the first and second radiation sources 20, 30 may be activated sequentially and/or simultaneously. Thus, the steps below, including imaging, image processing, image-based pre-delivery steps, and treatment delivery, although shown sequentially, may be executed simultaneously, including in real-time. Further, additional steps or fewer steps may be used.

It also will be appreciated that the imaging methods using the disclosed technology and described more fully below can be carried out using imaging from one or both of the first source of radiation 20 together with the first radiation detector 24 and the second source of radiation 30 together with the second radiation detector 34.

Figure 3:
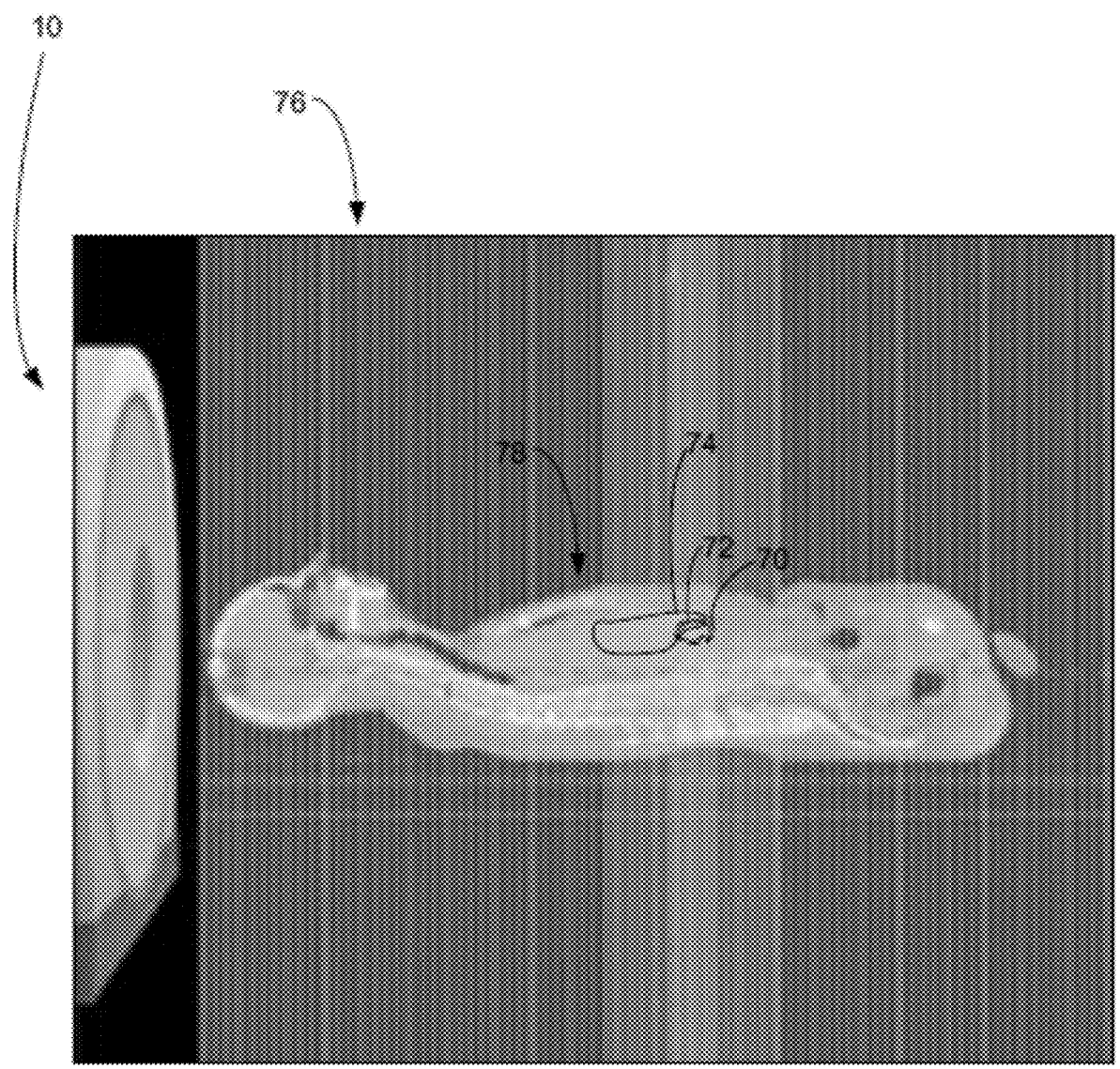
FIG. 3 is a diagrammatic illustration of an exemplary display and operator interface showing a slice of a planning image for use in association with the radiotherapy delivery device of FIG. 1.

Turning now to both FIGS. 2 and 3, the disclosed technology allows for control of at least the second radiation beam 32, such as via the controller 60, to modulate scan parameters of the second radiation beam 32 based on one or more parameters of the ROI (shown generally at 70). In other embodiments, depending on the use of the disclosed technology, scan parameters relative to one or both of the first radiation beam 22 or the second radiation beam 32 may be modulated based on one or more parameters of the ROI.

Looking to FIG. 3, an exemplary ROI 70 may include the pancreas 72 and the liver 74. In FIG. 3, these organs are viewable in a slice 76 (e.g., a sagittal slice) of a scan image. The slice 76 illustrates one exemplary user-selectable slice from a planning image (or other prior or previously-acquired image, including, but not limited to, an image acquired during an IGRT procedure), with the particular exemplary illustrated view being parallel to the patient's sagittal plane. A ROI for a patient 78 may include a volume of interest (VOI), such as a volume to target, which in this case may be the pancreas 72. A ROI further may include an organ at risk (OAR) (or portion of an organ at risk), which in the depiction may be a portion or all of the liver 74 (the gall bladder, not shown, also may be an OAR, for example). As such, a ROI may include numerous portions for which scan parameters are varied, depending on the view angle. With respect to the depicted embodiment, an imaging or radiotherapy plan may include targeting the pancreas 72 (VOI), while reducing or avoiding as much as possible exposure to the liver 74 (OAR). A ROI also may include a planning target volume (PTV), a geometric concept of a volume that may include portions of both the pancreas 72 and the liver 74, in the depicted ROI 70. The PTV may be sized to account for typical variations, deviations, or uncertainties in radiation delivery. In various embodiments, a ROI may include one or more of a VOI, PTV and OAR. These aspects of a ROI each may be of interest to imaging, since the requirement for image quality typically are higher in these regions, particularly in service of patient setup and adaptive treatment methods.

Figure 4:
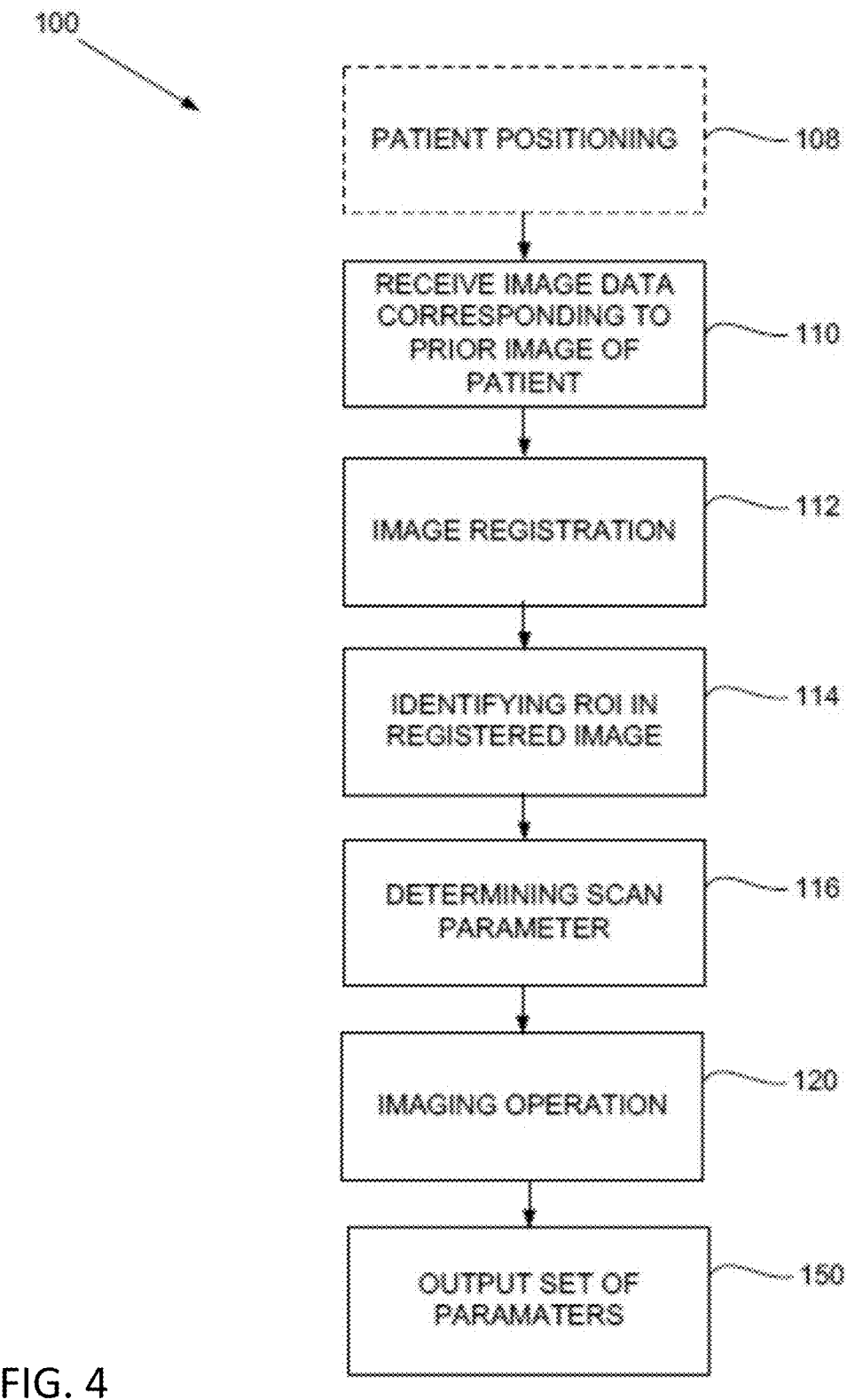
FIG. 4 is a diagrammatic representation of an imaging method in accordance with one aspect of the disclosed technology.

Turning next to FIG. 4, an exemplary imaging method 100 according to an embodiment is provided. With respect to a ROI, such as the ROI 70, acquisition plans and scan parameters can be initially set or further optimized based on one or more aspects of a ROI or portion of a ROI. Such aspects can include volume, density, contours, position relative to isocenter, position relative to a radiation output of a radiation delivery device, position relative to the whole body of the patient, or various other dimensions. Modulation of scan parameters may be varied depending on a view angle of the ROI, such as from a portion of the radiation-delivery device, with the intent of one or more of providing targeted exposure, providing uniformly disturbed exposure at a plurality of view angles, and reducing exposure where possible or non-necessary. Take for example a VOI of a ROI, where the VOI is offset from isocenter. Exposure modulation can be used to reduce radiation dose or turn off a radiation source while the VOI is unilluminated, essentially for half of a full rotation of a rotating gantry having about a 360-degree rotation. As will be further detailed, while many scan parameters or optimizations of scan parameters can be determined and entered manually, such as via the display 52 or operator interface 48, other scan parameters or optimizations of already determined/calculated scan parameters can be automatically provided via the imaging method 100.

It will be appreciated that the imaging method can include a CT imaging method in conjunction with an IGRT procedure in which a patient image can be captured before and/or during a treatment procedure. In such an exemplary case, the prior or otherwise previously-acquired image could be a planning image. Alternatively, the imaging method described in connection with FIG. 4 can be conducted independent of an IGRT application.

The method 100 is illustrated by a series of blocks. However, the methodologies are not limited by the order of the blocks, as some blocks can occur in different orders or concurrently with other blocks from that shown or described, such as in parallel or in series with other blocks. Moreover, less than all of the illustrated blocks may be required to implement an example methodology. Furthermore, other methodologies can employ additional or alternative, non-illustrated blocks.

The imaging method 100 starts at block 110 where image data corresponding to a prior or otherwise previously-acquired input image of a patient is received or obtained. In accordance with one embodiment, the received image data can be a prior CT image, such as a planning image. Alternatively, the received image can be from another imaging modality (e.g., a magnetic resonance (MR) image or ultrasound image). In accordance with one embodiment, the received image data can be CT image data from a prior planning image collected for use with and in connection with an IGRT procedure. The prior image can also simply be any image of the patient and ROI during any previous IGRT procedure performed, for example, an IGRT procedure performed on the immediately previous day. A suitable planning image, whether or not collected in connection with an IGRT procedure, may be a kV CT image, an x-ray image, a MV CT image, and/or a MR image.

The received input image includes at least one ROI, upon which parameters of further scanning or imaging will be based. The ROI may include one or more of a VOI, PTV or an OAR.

Once the received input image including the ROI is available, the received input image is registered to the patient at block 112. With respect to CT imaging, registration typically occurs between the planning image (received input image) and the current patient and the patient's location on the support 18. As mentioned above, the patient may be subject to an IGRT procedure. Registration may include comparison of two or more previously-acquired images or may include acquiring one or more additional scout projections of the patient while presently on support 18, for example. Because scan parameter determination/calculation/optimization is yet to be completed, in some embodiments the registration may be a rough registration that is less than fully accurate, but is at least suitably sufficient for identifying the ROI and its location in the patient relative to the whole patient body on the patient support 18.

After registration, at the next block 114, the ROI in the registered image is identified. The registered image may be a registered input image or another registered image. As used herein, an image includes data for constructing one or more slices or views of a total image, which also may be referred to as a scan.

Based on the ROI in the registered image, such as based on one or more of the aforementioned ROI parameters, at least one scan parameter is determined or generated for use in the current imaging operation 120 that will optimize the imaging operation 120. An optimized set of parameters for use during the imaging operation 120 can include data for one or more of the determined or generated scan parameters. This occurs in block 116 and is based on software or logic that can be set or programmed in controller 60. The determination may include manual and/or automatic input, calculation, and/or optimization of an already previously-determined parameter. The determined scan parameter (also may be referred to as an imaging parameter or scanning parameter) may be utilized in performance of a forward projection for the patient.

In some embodiments, one determined scan parameter may be exposure control, or more specifically a configuration of view angle dependent collimation that is calculated. Another determined scan parameter may be varying the speed of the support 18 during various portions of the scanning operation 120, so as to reduce radiation exposure to sensitive or non-relevant areas of the body, such as eyes or limbs, respectively. The actual scan parameter used for optimization does not have weight or precedence over any other scan parameter, but any of the parameters described herein may be used or determined for optimization of a particular scan. Moreover, the scan may already be at optimum condition and optimization of any or all of the parameters may not be required or determined for a particular scan.

Another scan parameter is beam collimation/filtration via a beamformer. The view angle dependent collimation may be calculated for one or more view angles, such as for a plurality of view angles. The configuration may be achieved via various methods, such as the use of a pre-patient filter, such as one or more of a dynamic bowtie filter, a jawed collimator assembly, or a multi-leaf collimator assembly. With such pre-patient filter, a major portion of a beam, such as the radiation beam 32 emitted by the second source of radiation 30, may be focused on a portion of the ROI. A peripheral portion of the patient outside of the ROI can be completely or partially collimated to aid in subsequent reconstruction processing.

Next, at block 120, an imaging operation is performed with respect to the patient and using the input image, which may be an input planning image, and also uses the determined scan parameter of block 116, to provide an image of the patient. Accordingly, the controller 60 may be configured to utilize the input image and determined scan parameter to perform the imaging operation.

Figure 5:
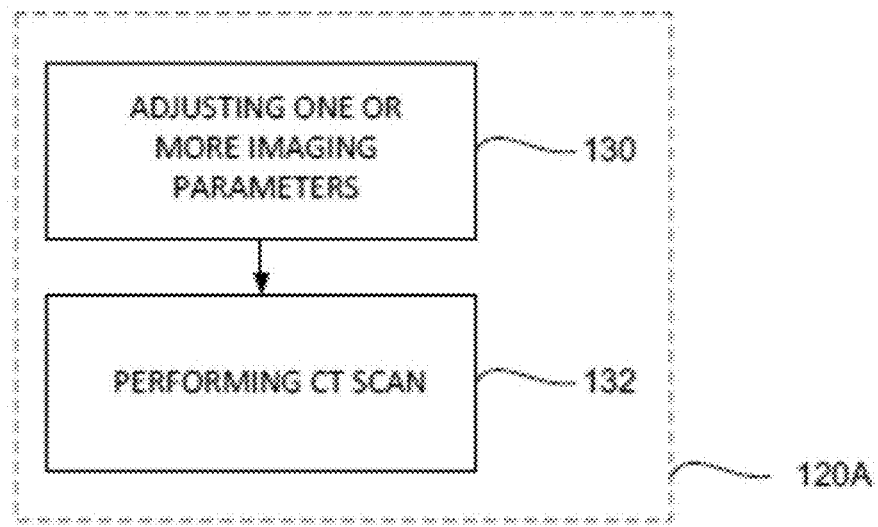
FIG. 5 is a diagrammatic representation of a portion of the imaging method of FIG. 4.

As depicted at FIG. 5, performing the imaging operation (identified as box 120A and insertable as block 120 of FIG. 4) may include performing a CT scan at block 132, such as a continuous helical fan beam CT scan of the patient. In some embodiments, the forward projection may be associated with an IGRT procedure. The performance of the CT scan may include adjusting one or more imaging parameters at block 130. The adjustment may be selective, automatic, or a combination thereof. The one or more imaging parameters, to be discussed in detail below, may be adjusted for one or more viewing angles, such as a plurality of viewing angles, based on one or more parameters of the respective ROI.

Figure 6:
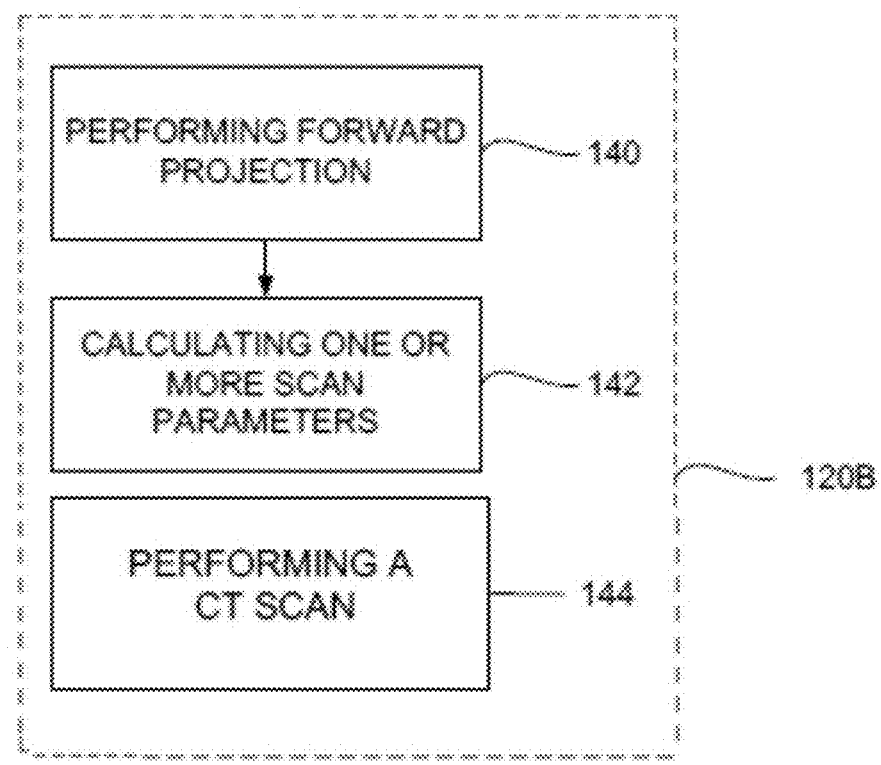
FIG. 6 is another diagrammatic representation of a portion of the imaging method of FIG. 4.

As alternatively depicted at FIG. 6, performing the imaging operation (identified as box 120B and insertable as block 120 of FIG. 4) may include performing a forward projection with respect to the patient at block 140. The forward projection uses the input image, which may be an input planning image, and also uses the determined scan parameter of block 116, to provide an image of the patient. The forward projection is performed for at least one view angle of the ROI, but alternatively may be performed for a plurality of view angles of the ROI to form a "curve" of parameter data for the ROI.

At block 142, for a given reference radiation dose to the patient, or to the ROI of the patient, one or more scan parameters are calculated. Calculating the one or more scan parameters may include initial calculation or optimization of previously determined parameters. Calculating one or more scan parameters includes calculating at least one additional scan parameter, beyond the parameter previously determined at block 116. In some embodiments, calculating one or more scan parameters includes re-calculating or optimizing the previously determined parameter that was previously determined at block 116. The one or more scan parameters, to be discussed in detail below, are calculated for at least one view angle of the ROI, but alternatively may be performed for a plurality of view angles of the ROI to form a "curve" of parameter data for the ROI. For a different dose level, a relation to the reference dose may be determined/calculated, and the one or more parameters adjusted accordingly. The CT scan is then performed in block 144.

Referring now to blocks 116 and 132/142, at which scan parameters are provided, the CT imaging and/or forward projection is configurable based on the ROI in terms of, but not limited to, tube spectrum, tube potential, tube current, beam filters, detector properties, focal spot, beam width, helical pitch, detector readout section size, etc. One or more of these configurations is adjusted via the determined, generated, calculated, or optimized scan (or image) parameters, collectively referred to as scan parameters or optimized set of parameters, at blocks 116 and 130/142 to enable the radiation exposure to the patient to best match user input relative to the ROI and parameters of the ROI.

The scan parameters determined may include exposure control, such as view angle dependent collimation or other beam collimation, as discussed above. As used herein, determining may include generating, calculating, and/or optimizing. As indicated, a pre-patient beam filter may be used. The beam filter may be selected in conjunction with tube potential parameters, such as to provide an optimum radiographic contrast for a portion of the ROI.

Additional scan parameters associated with the beam may include pulse rate of the beam and beam energy, where the beam energy may be in the kV range, for example. Other exemplary scan parameters are tube current and tube pulse width. The tube current of a scan multiplied by the tube pulse width is proportional and determinative of the number of photons in a scan beam. A curve of the photon output of an x-ray tube which has the photon output on the vertical axis with the horizontal axis indicative of view angles at a particular time can be generated and modified by optimization of these various scan parameters.

The scan parameters determined may include a speed of the patient support 18, such as adjustment of a linear speed of the patient support 18 relative to, such as through, the rotatable gantry 12. The scan parameters determined may include a scan pitch, such as with respect to a helical scan. Scan pitch may be defined with respect to a single slice or multislice CT. The scan parameters determined may include a movement distance of the patient, such as a linear distance traveled relative to a starting location relative to the rotatable gantry 12.

The scan parameters determined may be associated with a radiation detector, such as the detector 34. These scan parameters may include detector gain and/or detector binning. Selection of a detector readout section may be another parameter for consideration. Choices may include, for example, full panel readout, half panel readout, ⅓ panel readout, ⅔ panel readout, etc. Choice of the detector readout section can be dependent on scan speed, beam collimator, helical pitch, etc. Gain may be based on radiation source tube potential, radiation source tube current, patient size, and/or scan speed. Tube potential adjustment may allow for optimum contrast, contrast-to-noise ratio (CNR) and/or minimizing patient dose, for example, to obtain optimum soft tissue contrast or to optimize projection data where the patient has a metal implant. Tube current is adjustable for optimizing gray level and/or limiting quantum noise. As a result of at least tube potential and tube current adjustments, a gray level may be adjusted, such as to limit or altogether avoid saturation or photon starvation. Binning can allow charges from adjacent pixels to be combined, such as to optimize data streaming speed and/or noise. Focal spot may be adjustable according to varying of one or more of the tube current, tube potential and scan speed. Other parameters can include beam width (e.g., dynamically collimated from view to view), helical pitch (e.g., dynamic helical pitch from view to view), and detector readout section size (e.g., dynamic selection of detector readout section from view to view).

Any of the aforementioned scan parameters may be determined on a slice-by-slice basis in a longitudinal direction of patient movement for one or more view angles, such as for a plurality of view angles. For example, the slice-by-slice determination may be applicable to a fan-beam shaped radiation source, such as with respect to implementation of IGRT.

Returning now to FIG. 4, after an imaging operation is performed at block 120, a set of one or more scan parameters (e.g., an optimized set of parameters) is output at block 150. The set includes at least one determined or calculated scan parameter, referring to block 116 and 130/142. Preferably, the set includes each of the scan parameters determined and/or calculated at each of blocks 116 and 130/142. Accordingly, the set includes at least one view-angle dependent modulated scan parameter based on the ROI or portion of the ROI, such as based on one or more parameters of the ROI or portion of the ROI.

Additionally, as depicted as a dashed line block at FIG. 4, one or more method embodiments may include an additional step of patient positioning at block 108. While shown as the initial step, block 108 may be otherwise positioned before block 120. At block 108, the patient subject to an image acquisition or IGRT is positioned on a patient support/couch, such as the patient support 18, that is configured for longitudinal movement within a rotatable gantry, such as the rotatable gantry 12. The rotatable gantry will be coupled to a source of radiation and to a detector positioned to receive radiation from the source of radiation. The source of radiation may be a kV source configured to emit a fan beam, such as the second source of radiation 30.

In summary, the disclosed technology may allow for recognition of one or more benefits associated with a radiation delivery device and method using ROI guidance for controlling exposure of a beam from a source of imaging radiation of the radiation delivery device based on one or more parameters of a ROI of a patient. As previously mentioned, these benefits may include, but are not limited to, one or more of reduced scan time, targeted dosing, uniform dosing relative and reduced radiation exposure to the patient or ROI of the patient and/or reduced x-ray scatter with improved soft tissue contrast. The reduced radiation exposure will prevent damage to sensitive organs such as eyes and other organs not involved with the ROI. Another benefit of the disclosed technology is that an x-ray dosage can be optimized to enhance image quality to obtain better quality and more precise images for treatment scans.

In further summary, a device 10 is provided that is configurable to provide controlled exposure of a beam 22, 32 from a source of imaging radiation 20, 30 of a radiation-delivery device 10 based on one or more parameters of a ROI of a patient. It will be appreciated that the above-described radiation-delivery technology (device and method) can generate low-energy (e.g., kV) images that can be used in a variety of ways without departing from the scope of the disclosed technology. For example, images generated by the radiotherapy device can be used to align a patient prior to treatment. In accordance with other exemplary use cases, images generated by the radiotherapy device can be used to calculate imaging dose. In accordance with another exemplary use case, images generated by the radiotherapy device can be used to calculate treatment dose.

Also provided is a method of scanning parameter optimization, which method may be useful with IGRT, allows for controlling exposure of a beam from a source of imaging radiation of a radiation-delivery device based on one or more parameters of a ROI of a patient. The one or more parameters of the ROI may include a dimension, outer contour, density, location relative to an outlet of the beam, location relative to isocenter, and relative location with respect to the patient's entire body. Exposure of the patient to the beam may be varied via modulation of one or more scanning parameters for controlling an aspect of the beam to provide for targeted and or reduced radiation exposure of the patient or portion of the patient. The modulation may be varied depending on a view angle of the ROI from a portion of the radiation-delivery device, which view angle may vary upon movement of the ROI and/or a radiation delivery portion of the device relative to one another.

Figure 7:
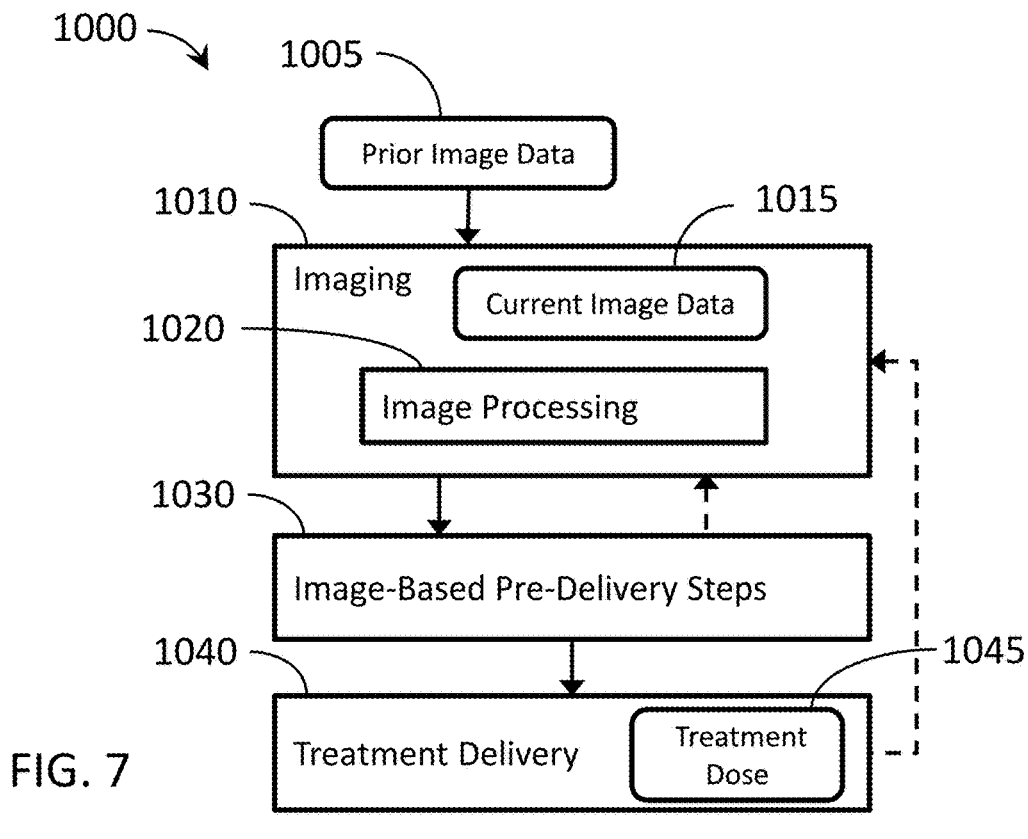
FIG. 7 is a flow chart depicting an exemplary method of IGRT using a radiotherapy device.

FIG. 7 is a flow chart depicting an exemplary method 1000 of IGRT using a radiotherapy device (e.g., radiotherapy device 10). Prior image data 1005 of the patient is available for use (e.g., a prior image, which may be a previously-acquired planning image, including a prior CT image, as discussed above). Prior data 1005 can also include treatment plans, phantom information, models, a priori information, etc. In some embodiments, prior image data 1005 is generated by the same radiotherapy device, but at an earlier time. At step 1010, imaging of the patient is performed using a source of low-energy radiation (e.g., kV radiation from second radiation source 30). Step 1010 can produce image(s) or imaging data 1015 (e.g., input data that includes the primary data acquired from the available source trajectory, as discussed above). In some embodiments, image quality may be adjusted to optimize a balance between image quality/resolution and dosage. In other words, not all images need to be of the highest quality or image quality may be adjusted to optimize or trade off a balance between image quality and image acquisition time. Imaging step 1010 also includes image processing to generate patient images based on the imaging data (e.g., in accordance with method 100 described above). Although image processing step 1020 is shown as part of imaging step 1010, in some embodiments image processing step 1020 is a separate step, including where image processing is executed by separate devices.

Next, at step 1030, one or more image-based pre-delivery steps, discussed below, are performed based at least in part on the imaging data 1015 from step 1010. As discussed in more detail below, step 1030 can include determining various parameters associated with the therapeutic treatment and (subsequent) imaging planning. Step 1030 also may include the data optimization process based on an ROI discussed above with respect to FIGS. 3-6. In some embodiments, image-based pre-delivery steps (1030) may require more imaging (1010) before treatment delivery (1040). Step 1030 can include adapting a treatment plan based on the imaging data 1015 as part of an adaptive radiotherapy routine. In some embodiments, image-based pre-delivery steps 1030 may include real-time treatment planning. Embodiments may also include simultaneous, overlapping, and/or alternating activation of the imaging and therapeutic radiation sources. Real-time treatment planning may involve any or all of these types of imaging and therapeutic radiation activation techniques (simultaneous, overlapping, and/or alternating).

Next, at step 1040, therapeutic treatment delivery is performed using a source of high-energy radiation (e.g., MV radiation from first radiation source 20). Step 1040 delivers a treatment dose 1045 to the patient according to the treatment plan. In some embodiments, the IGRT method 1000 may include returning to step 1010 for additional imaging at various intervals, followed by image-based pre-delivery steps (1030) and/or treatment delivery (1040) as required. In this manner the imaging data 1015 may be produced and utilized during IGRT using one radiotherapy device 10 that is capable of adaptive therapy. As mentioned above, steps 1010, 1020, 1030, and/or 1040 may be executed simultaneously, overlapping, and/or alternating.

IGRT can include at least two general goals: (i) to deliver a highly conformal dose distribution to the target volume; and (ii) to deliver treatment beams with high accuracy throughout every treatment fraction. A third goal can be to accomplish the two general goals in as little time per fraction as possible. Delivering treatment beams accurately requires the ability to identify and/or track the location of the target volume intrafraction with high-quality images. The ability to increase delivery speed requires the ability to accurately, precisely, and quickly move the radiation source according to the treatment plan.

Figure 8:
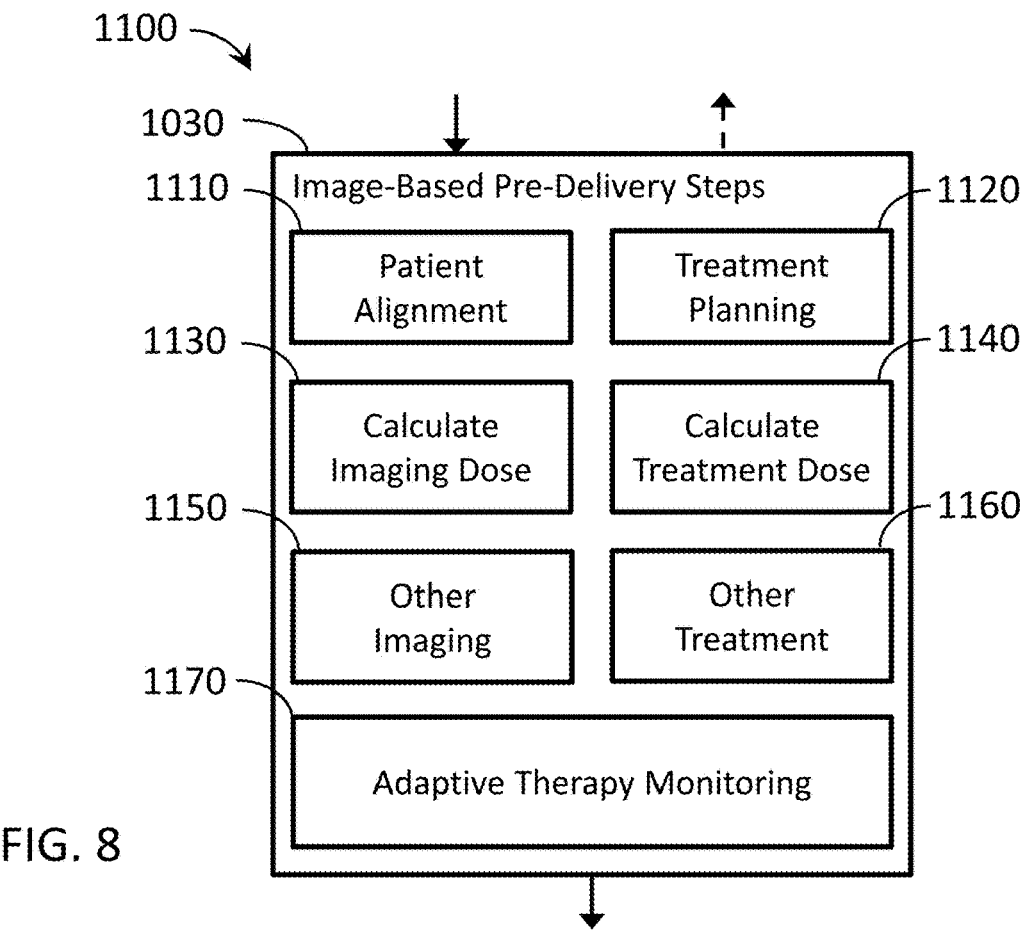
FIG. 8 is a block diagram depicting exemplary image-based pre-delivery steps.

FIG. 8 is a block diagram 1100 depicting exemplary image-based pre-delivery steps/options that may be associated with step 1030 above. It will be appreciated that the above-described radiotherapy device (e.g., radiotherapy device 10) can generate kV images that can be used in a variety of ways, including for image-based pre-delivery steps (1030), without departing from the scope of the present invention. For example, images 1015 generated by the radiotherapy device can be used to align a patient prior to treatment (1110). Patient alignment can include correlating or registering the current imaging data 1015 with imaging data associated with earlier pre-treatment scans and/or plans, including the treatment plan. Patient alignment can also include feedback on the physical position of the patient relative to the radiation source to verify whether the patient is physically within the range of the delivery system. If necessary, the patient can be adjusted accordingly. In some embodiments, patient alignment imaging may purposely be of lesser quality to minimize dosage but provide adequate alignment information.

Images generated by the radiotherapy device can also be used for treatment planning or re-planning (1120). Optimization for the treatment plan can also be provided by the process described in FIGS. 2-6 above. For example, the optimized data can be used to determine exposure locations and speeds during treatment using the patient support 18 and radiation source 20. In such instances, scan times can be optimized so that certain portions of the body are excluded from treatment by speed of the patient support or wider collimation of the beam. Similar advantages can be obtained by changing the part of the scan in a helical context. In various embodiments, step 1120 can include confirming the treatment plan, modifying the treatment plan, generating a new treatment plan, and/or choosing a treatment plan from a set of treatment plans (sometimes referred to as "plan of the day"). For example, if the imaging data 1015 shows that the target volume or ROI is the same as when the treatment plan was developed, then the treatment plan can be confirmed. However, if the target volume or ROI is not the same, re-planning of the therapeutic treatment may be necessary. In the case of re-planning, because of the high quality of the imaging data 1015 (generated by the radiotherapy device 10 at step 1010), the imaging data 1015 may be used for treatment planning or re-planning (e.g., generating a new or modified treatment plan). In this manner, pre-treatment CT imaging via a different device is not necessary. In some embodiments, confirming and/or re-planning may be an ongoing procedure before and/or after various treatments.

In accordance with another exemplary use case, images generated by the radiotherapy device 10 can be used to calculate imaging dose (1130), which may be used for ongoing determinations of total dose to the patient and/or for subsequent imaging planning. Step 1130 also may include the data optimization method based on an ROI discussed above with respect to FIGS. 3-6. The quality of subsequent imaging may also be determined as part of the treatment planning, for example, to balance quality and dosage. In accordance with another exemplary use case, images generated by the radiotherapy device 10 can be used to calculate treatment dose (1140), which may be used for ongoing determinations of total dose to the patient and/or may be included as part of treatment planning or re-planning.

In accordance with other exemplary use cases, images generated by the radiotherapy device 10 can be used in connection with planning or adjusting other imaging (1150) and/or other treatment (1160) parameters or plans, including, for example, as part of adaptive therapy and/or treatment plan generation. In accordance with another exemplary use case, images generated by the radiotherapy device 10 can be used in connection with adaptive therapy monitoring (1170), which can include monitoring treatment delivery and adapting as required.

It should be appreciated that the image-based pre-delivery steps (1030) are not mutually exclusive. For example, in various embodiments, calculate treatment dose (1140) can be a step by itself and/or can be part of adaptive therapy monitoring (1170) and/or treatment planning (1120). In various embodiments, the image-based pre-delivery steps (1030) can be performed automatically and/or manually with human involvement.

Figure 9:
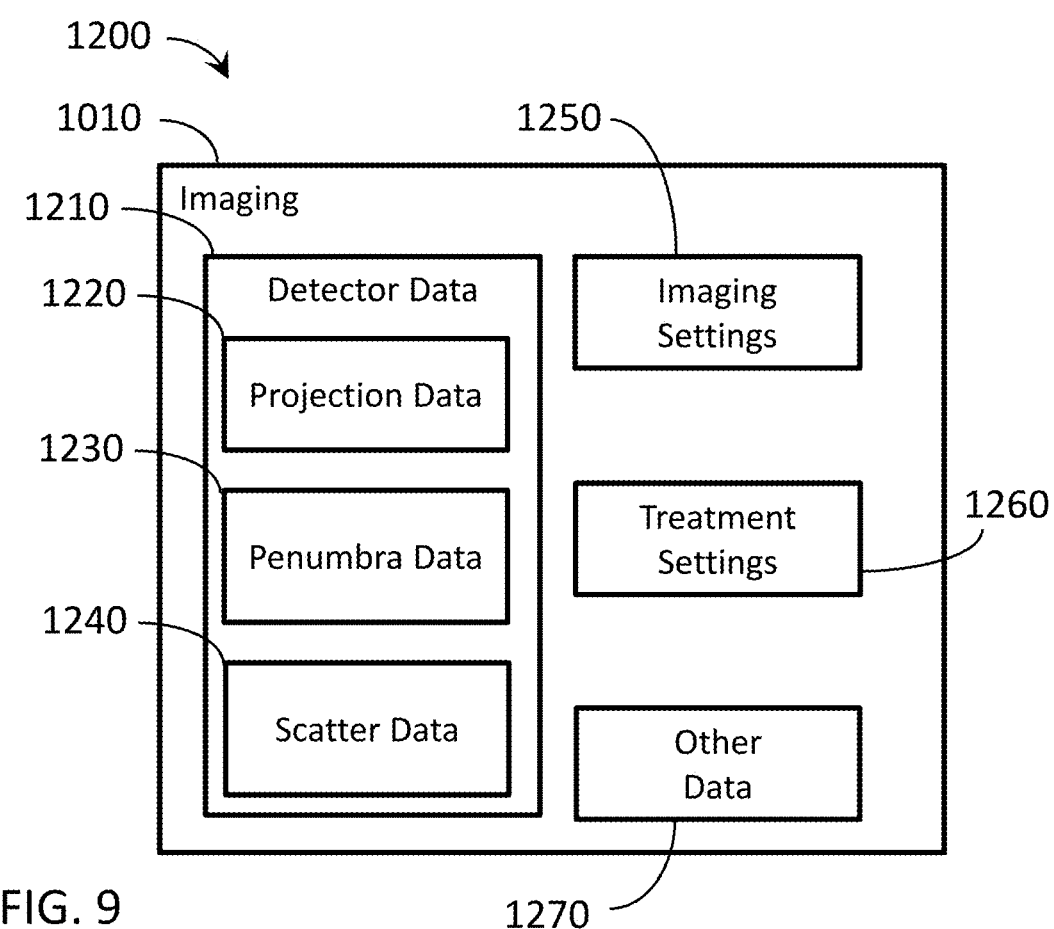
FIG. 9 is a block diagram depicting exemplary data that may be utilized during imaging or image-based pre-delivery steps.

FIG. 9 is a block diagram 1200 depicting exemplary data sources that may be utilized during imaging (1010) and/or subsequent treatment planning (1020), in addition to the prior data 1005. Detector data 1210 represents the data received by the image radiation detector 34. The projection data 1220 is the data generated by the radiation incident in the collimated beam area, which may be referred to as the primary region. The penumbra data 1230 is the data generated by the radiation incident in the penumbra region or area. The scatter data 1240 is the data generated by the radiation incident in a peripheral or scatter (only) region or area.

The penumbra data 1230 and/or the scatter data 1240 may be utilized to improve the quality of the images generated by the imaging step 1010. In some embodiments, the penumbra data 1230 and/or the scatter data 1240 may be combined with the projection data 1220 and/or analyzed in view of the applicable imaging settings 1250, treatment settings 1260 (e.g., if simultaneous imaging and treatment radiation), and any other data 1270 associated with the radiotherapy device 10 at the time of the data collection at the imaging detector 34, including as discussed above. In other embodiments, the data may be used for the treatment planning step 1020.

Although the disclosed technology has been shown and described with respect to a certain aspect, embodiment or embodiments, it is obvious that equivalent alterations and modifications will occur to others skilled in the art upon the reading and understanding of this specification and the annexed drawings. In particular regard to the various functions performed by the above described elements (components, assemblies, devices, members, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary aspect, embodiment or embodiments of the disclosed technology. In addition, while a particular feature of the disclosed technology may have been described above with respect to only one or more of several illustrated aspects or embodiments, such feature may be combined with one or more other features of the other embodiments, as may be desired and advantageous for any given or particular application.

While the embodiments discussed herein have been related to the systems and methods discussed above, these embodiments are intended to be exemplary and are not intended to limit the applicability of these embodiments to only those discussions set forth herein. While the present invention has been illustrated by the description of embodiments thereof, and while the embodiments have been described in some detail, it is not the intention of the applicant to restrict or in any way limit the scope of the appended claims to such detail. Additional advantages and modifications will readily appear to those skilled in the art.

Therefore, the invention in its broader aspects is not limited to the specific details, representative apparatus and methods, and illustrative examples shown and described. Accordingly, departures may be made from such details without departing from the spirit or scope of the applicant's general inventive concept.

The invention claimed is:

1. An imaging method for use with image-guided radiation therapy (IGRT) of a patient, the method comprising:
   receiving image data corresponding to a prior image of the patient, wherein the image data includes data corresponding to a region of interest (ROI);
   obtaining projection image data of the patient;
   performing an image reconstruction based on the obtained projection image data of the patient to obtain a patient image;
   registering the prior image with the obtained patient image to obtain a registered image;
   identifying the ROI in the registered image;
   projecting ROI image data based on the prior image;
   generating an optimized set of parameters using the projected ROI image data, the optimized set of parameters optimized to at least one of reduce scan time of a CT scan of the patient, target radiation dose to a particular area of the patient, unformalize dosing to the particular area of the patient, reduce radiation exposure to the patient, reduce radiation exposure to the ROI, reduce x-ray scatter, and improve soft tissue contrast;
   performing the CT scan of the patient using said optimized set of parameters.

2. The method of claim 1, wherein the step of projecting ROI image data is also based on the registered image.

3. The method of claim 1, wherein the optimized set of parameters comprises data for modulation of tube current when imaging the patient.

4. The method of claim 1, wherein the optimized set of parameters comprises data for adjusting tube potential when imaging the patient.

5. The method of claim 1, wherein the optimized set of parameters comprises data corresponding to scan speed when imaging the patient.

6. The method of claim 1, wherein the optimized set of parameters comprises data corresponding to detector gain.

7. The method of claim 1, wherein the optimized set of parameters comprises data corresponding to detector binning.

8. The method of claim 1, wherein the optimized set of parameters comprises data corresponding to at least one of a focal spot of an imaging beam, an imaging beam width, a helical pitch of an imaging scan, or a detector readout section size during imaging.

9. The method of claim 1, wherein the optimized set of parameters comprises data corresponding to radiographic contrast for various areas of the patient's body.

10. The method of claim 1, wherein the optimized set of parameters comprises data corresponding to thickness or material of an imaging beam filter.

11. The method of claim 1, wherein the optimized set of parameters comprises data corresponding to x-ray dosage of the imaging beam.

* * * * *